United States Patent [19]
Gerwick et al.

[11] Patent Number: 6,057,348
[45] Date of Patent: May 2, 2000

[54] CURACIN A ANALOGS EXHIBITING ANTIPROLIFERATIVE ACTIVITY AGAINST CELLS

[75] Inventors: William H. Gerwick, Corvallis, Oreg.; John R. Falck, Dallas, Tex.; Brian L. Marquez, Corvallis, Oreg.

[73] Assignee: Oregon State University, Corvallis, Oreg.

[21] Appl. No.: 09/115,582

[22] Filed: Jul. 14, 1998

Related U.S. Application Data

[60] Provisional application No. 60/052,467, Jul. 14, 1997.
[51] Int. Cl.[7] ....................... C07D 277/24; A61K 31/427
[52] U.S. Cl. ............................................ 514/365; 548/203
[58] Field of Search ............................... 548/203; 514/365

[56] References Cited

PUBLICATIONS

Verdier–Pinard Mol. Pharm. 53(1) 62 1998, Jan. 1998.
Nagle et al., "Absolute Configuration of Curacin A, a Novel Antimitotic Agent from the Tropical Marine Cyanobacterium *Lyngbya majuscula*," *Tetrahedron Letters*, vol. 36, No. 8, pp. 1189–1192 (1995).

*Primary Examiner*—Robert Gerstl
*Attorney, Agent, or Firm*—Klarquist Sparkman Campbell Leigh & Whinston, LLP

[57] ABSTRACT

Isomers of a cytotoxic compound isolated and purified from a marine cyanobacterium *Lyngbya majuscula* are disclosed. The compound, termed "curacin D", exhibits substantial biological activity against proliferating cells. Analogs of curacin A also are described, as are formulations that include curacin D and the curacin A analogs. The curacins A–D and analogs of curacin A exhibit antimitotic behavior.

10 Claims, 15 Drawing Sheets

FIG. 1A
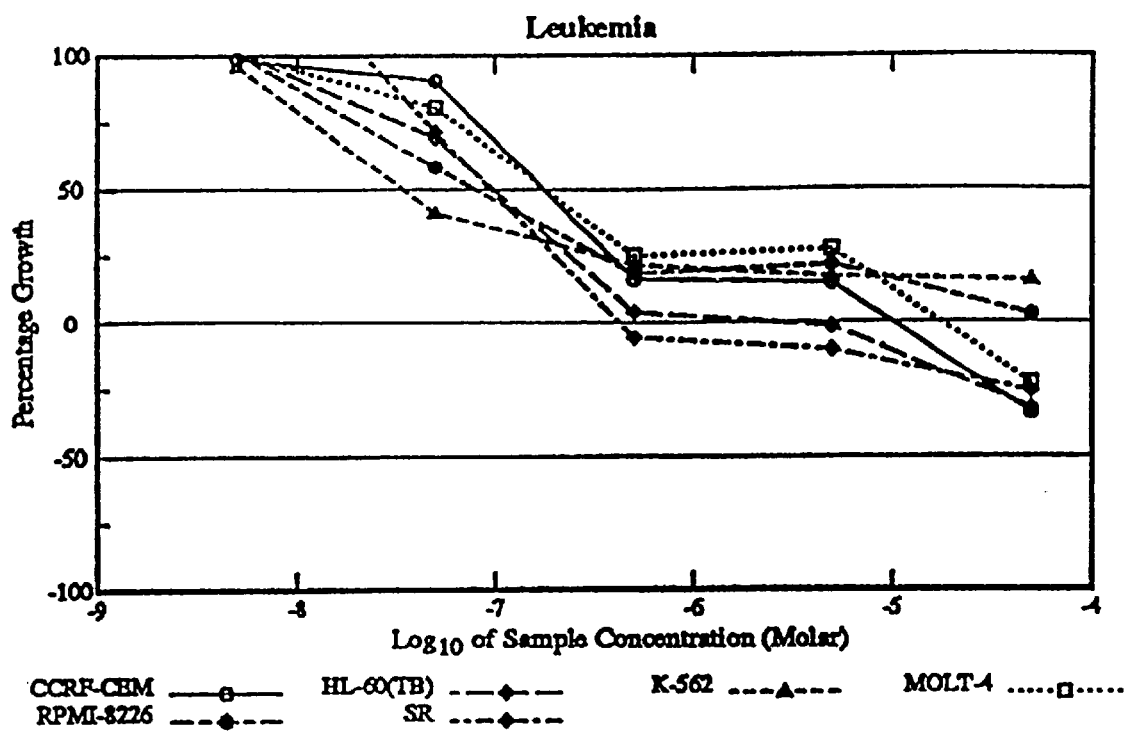
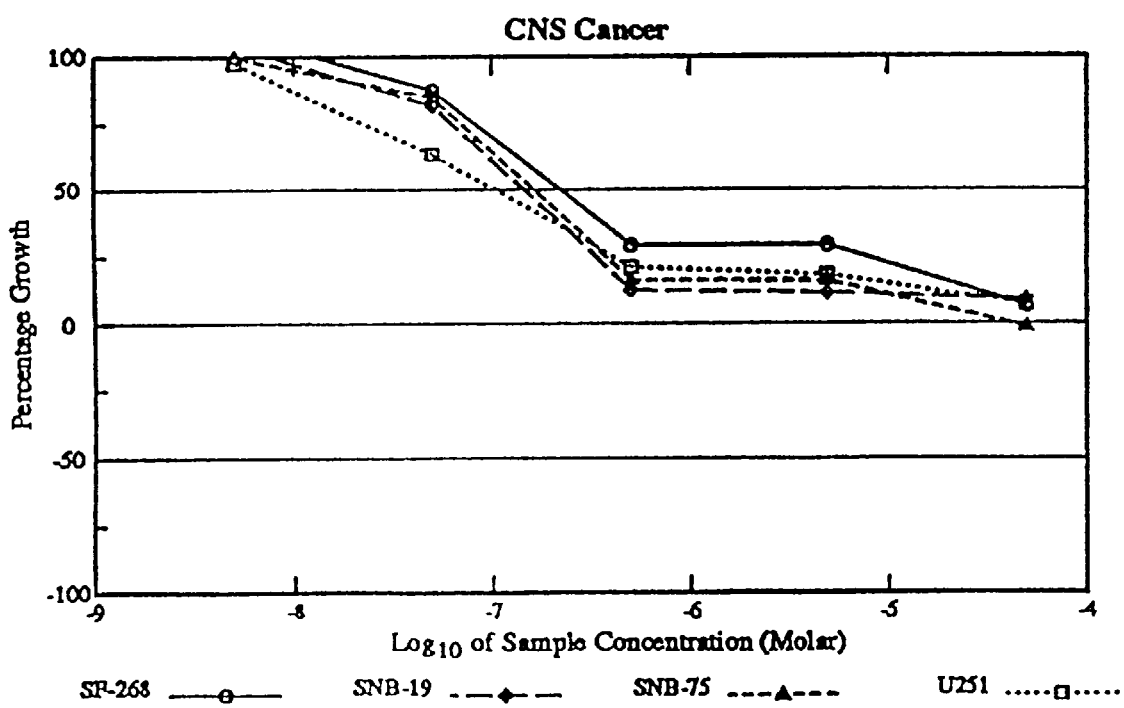
FIG. 1B

FIG. 1C
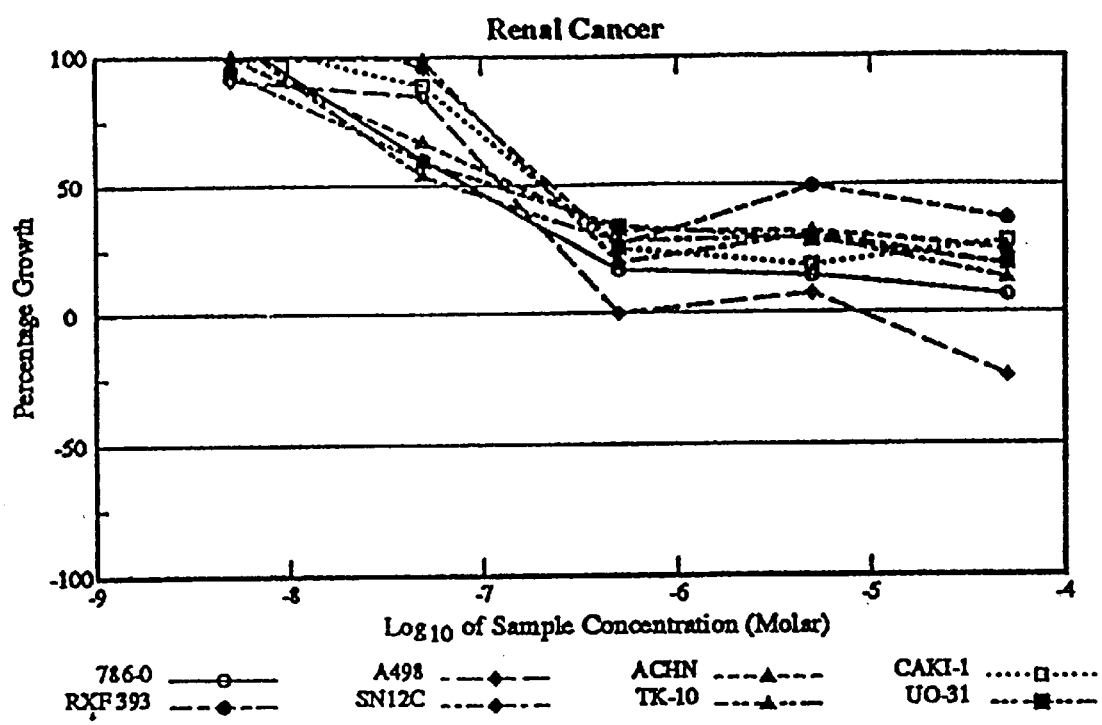
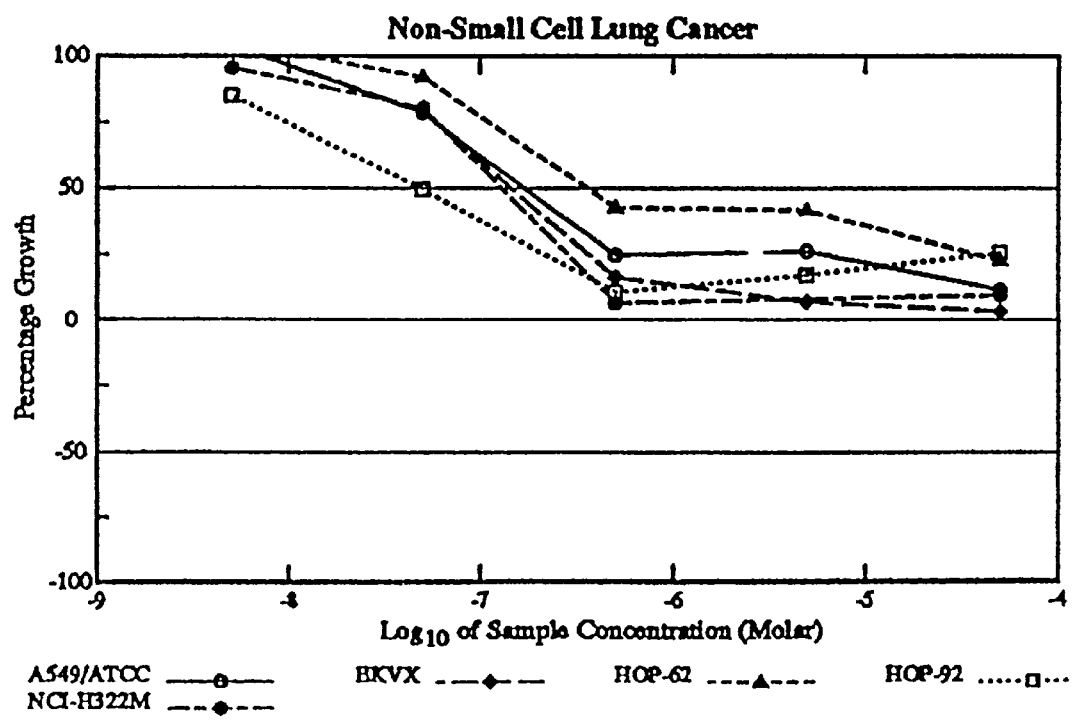
FIG. 1D

CURACIN A ANALOGS EXHIBITING ANTIPROLIFERATIVE ACTIVITY AGAINST CELLS

CROSS REFERENCE TO RELATED APPLICATION

This application claims priority from copending U.S. Provisional Patent Application No. 60/052,467, filed on Jul. 14, 1997, which is incorporated herein by reference.

ACKNOWLEDGEMENT OF GOVERNMENTAL SUPPORT

This invention was supported by the National Cancer Institute, National Institutes of Health, grant No. CA52955. The United States government may have certain rights in this invention.

FIELD OF THE INVENTION

This invention concerns naturally occurring curacin D and curacin A analogs that exhibit biological activity.

BACKGROUND OF THE INVENTION

Agents that inhibit cell growth are potentially useful for treating cancer. One such agent is curacin A. Originally purified as a major lipid component of a strain of the cyanobacterium *Lyngbya majuscula* isolated in Curacao, curacin A is a potent inhibitor of cell growth and mitosis, binding rapidly and tightly at the colchicine site of tubulin. See, U.S. Pat. No. 5,324,739 to Gerwick, which is incorporated herein by reference.

Although antimitotic agents, both natural products and synthetic compounds, display a wide structural diversity, virtually all of them interact with the α/β-tubulin dimer, the major component of microtubules. Hamel's "Interactions of Tubulin with Small Ligands," *Microtubule Proteins*, (CRC Press, 1990) and "Antimitotic Natural Products and Their Interactions with Tubulin," *Med. Res. Rev.*, 16:207–231 (1996). Most of these compounds inhibit microtubule assembly in cells and in cell-free systems. A major mechanism involved in the cytotoxic action of these drugs appears to be altered microtubule dynamics, and most drugs studied thus far reduce tubulin turnover at microtubule ends.

Net inhibitors of microtubule assembly largely fall into two classes. The first group consists of a variety of complex natural products that inhibit the binding of vinca alkaloids to tubulin and inhibit formation of an intra-β-tubulin cross link between cys12 and cys201/211. These natural products also interfere with GTP/GDP exchange on β-tubulin (vinca domain agents).

The second group of net inhibitors of microtubule assembly consists of numerous synthetic compounds and structurally simpler natural products, such as the cis-stilbene combretastatin A-4 and the estrogen metabolite 2-methoxyestradiol. These compounds inhibit the binding of colchicine to tubulin, inhibit formation of an intra-β-tubulin cross link between cys239 and cys354, have no effect on GTP/GDP exchange, and generally induce a GTPase reaction uncoupled from assembly (colchicine-site agents). A recurring structural theme in the colchicine-site agents has been at least one, and generally two aromatic, domains. Hamel, supra; and Luduena et al., "Tubulin Sulfhydryl Groups as Probes and Targets for Antimitotic and Antimicrotubule Agents," *Pharmac. Ther.*, 49:133–152 (1991).

Curacin A is a potent colchicine-site antimitotic agent, and is a major exception to structural generalizations stated above in that it has no aromatic residue. The compound inhibits microtubule assembly and, despite its unique structure, is a potent competitive inhibitor of the binding of colchicine to tubulin. Blokhin et al., "Characterization of the Interaction of the Marine Cyanobacterial Natural Product Curacin A with the Colchicine Site of Tubulin and Initial Structure-Activity Studies with Analogs," *Mol. Pharmacol.*, 48:523–531 (1995). Initial studies demonstrate that curacin A stimulated the uncoupled GTPase reaction typical of colchicine-site agents, and indirect observations were consistent with curacin A binding rapidly and dissociating slowly from tubulin. Id. Curacin A inhibits formation of the cys239-cys354 cross link in ,β-tubulin, Luduena et al., "Interaction of Curacin A with Bovine Brain Tubulin," *Mol. Biol. Cell*, 5:283a (1994). Moreover, curacin A also may have a relatively unusual effect on microtubule dynamics, in that low concentrations of the drug increase tubulin turnover at microtubule ends. Pack et al., "Curacin A, a New Potent Antimitotic Marine Natural Product, Increases Dynamic Instability of Microtubules, " *Proc. Amer. Assoc. Cancer Res.*, 36:455 (1995).

Gerwick's U.S. Pat. No. 5,324,739 and the references cited above demonstrate that curacin A is an important, biologically active material. Curacin A has, however, exhibited limited chemical stability, and appears to undergo chemical modification to a less biologically active compound when stored neat. See, "Note Added in Proof" at page 1245 of Gerwick et al., "Structure of Curacin A, a Novel Antimitotic, Antiproliferative, and Brine Shrimp Toxic Natural Product from the Marine Cyanobacterium *Lyngbya majuscula*," *J. Org. Chem.*, 1243–1245 (1994). Additional information, therefore, is needed about how to stabilize the biologically active curacin A structure, and likely the curacin B-curacin D structures as well. Additional information also is needed concerning the structure-activity characteristics of the naturally occurring curacins A–D, and analogs thereof.

SUMMARY OF THE INVENTION

The present invention is directed to a purified form of the naturally occurring and biologically active curacin D, as well as biologically active synthetic and/or semisynthetic analogs of curacin A. Curazole, one example of such a biologically active curacin A analog, comprises an aromatic thiazole ring instead of the thiazoline ring generally characteristic of the naturally occurring curacin A–D. The aromatic system of curazole appears to be much less susceptible to oxidation, a proposed reaction responsible for the observed chemical instability of curacin A.

Curazole analogs generally satisfy the formula

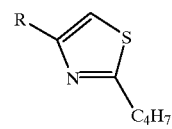

wherein R is selected from the group consisting of hydrogen and aliphatic chains having from 3 to about 15 carbon atoms. Such compounds generally include an R comprising an aliphatic chain having about 14 carbon atoms in the chain, and generally at least one double bond. Preferred embodiments of the compound generally include two or more double bonds, with two of the double bonds being conjugated dienes.

The R group of curazole also generally satisfies the formula

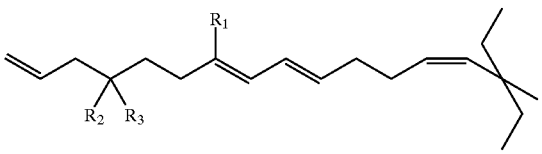

wherein $R_1$ is selected from the group consisting of hydrogen and lower alkyl, $R_2$ is selected from the group consisting of hydrogen, hydroxyl, lower alkyl, and lower alkoxy, $R_3$ is selected from the group consisting of hydrogen, hydroxyl, lower alkyl, and lower alkoxy, and wherein $R_2$ and $R_3$ also may be bonded together to form cyclic ring structures having from 3 to about 6 atoms in the ring.

The present invention also is directed to antiproliferative curacin A analogs having a formula

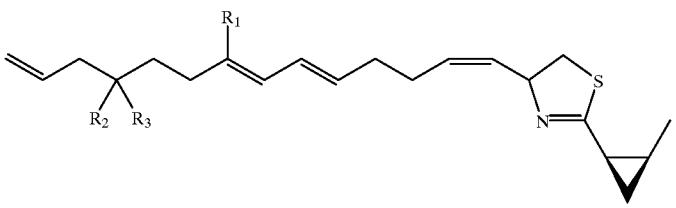

wherein $R_1$ is selected from the group consisting of hydrogen and lower alkyl chains. If $R_1$ is hydrogen then $R_2$ and $R_3$ are selected from the group consisting of hydrogen, hydroxyl, lower alkyl, and lower alkoxy. If $R_1$ is lower alkyl, then $R_2$ and $R_3$ are selected from the group consisting of hydrogen, hydroxyl, and methylmethoxy. $R_2$ and $R_3$ also can be bonded together to form ring structures having from about 3 to about 6 carbon atoms in the ring.

The compounds described herein can be formulated into compositions further comprising inert carriers, excipients, and other materials conventionally used in the formulation of pharmaceutical compositions. Moreover, such compounds and compositions may be administered to subjects to inhibit the proliferation of living cells.

BRIEF DESCRIPTION OF THE DRAWINGS

FIGS. 1A–1I are dose-response curves showing the effect of curazole on various cancer cell lines in culture, as set forth in Examples 4–63.

FIGS. 3A–3I are dose-response curves showing the effect of purified curazole on various cancer cell lines in culture, as set forth in Examples 64–123.

DETAILED DESCRIPTION OF THE PREFERRED EMBODIMENTS

Figure 1E:
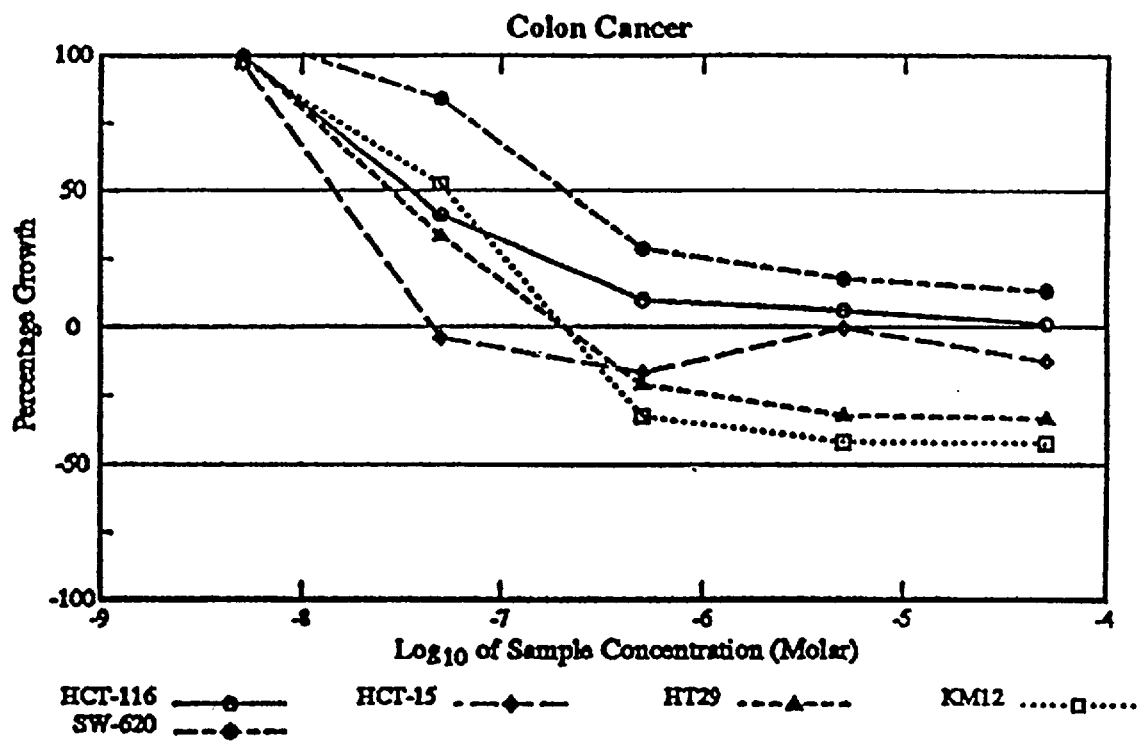
Figure 1F:
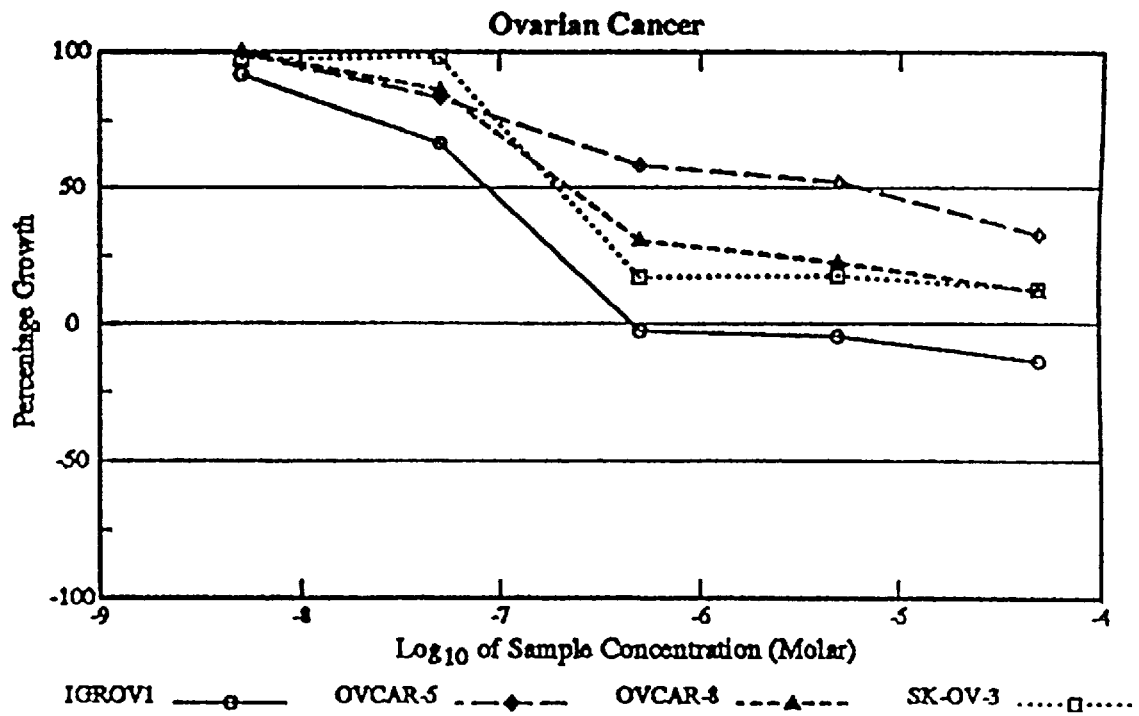
Figure 1G:
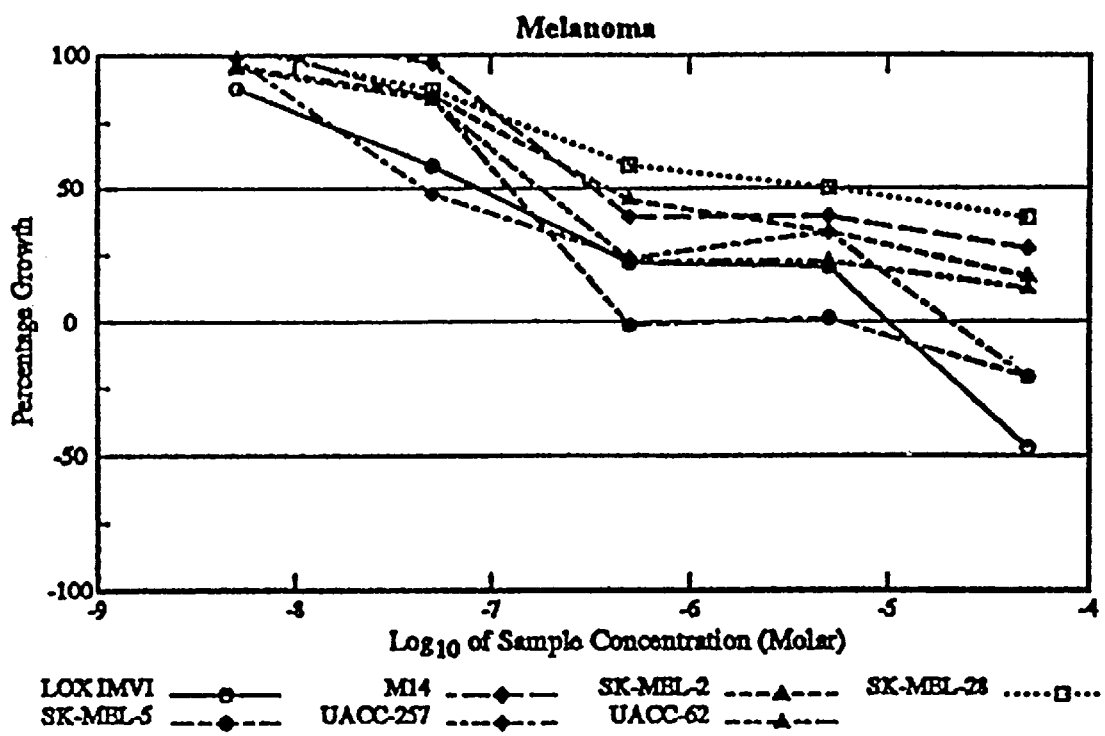
Figure 1H:
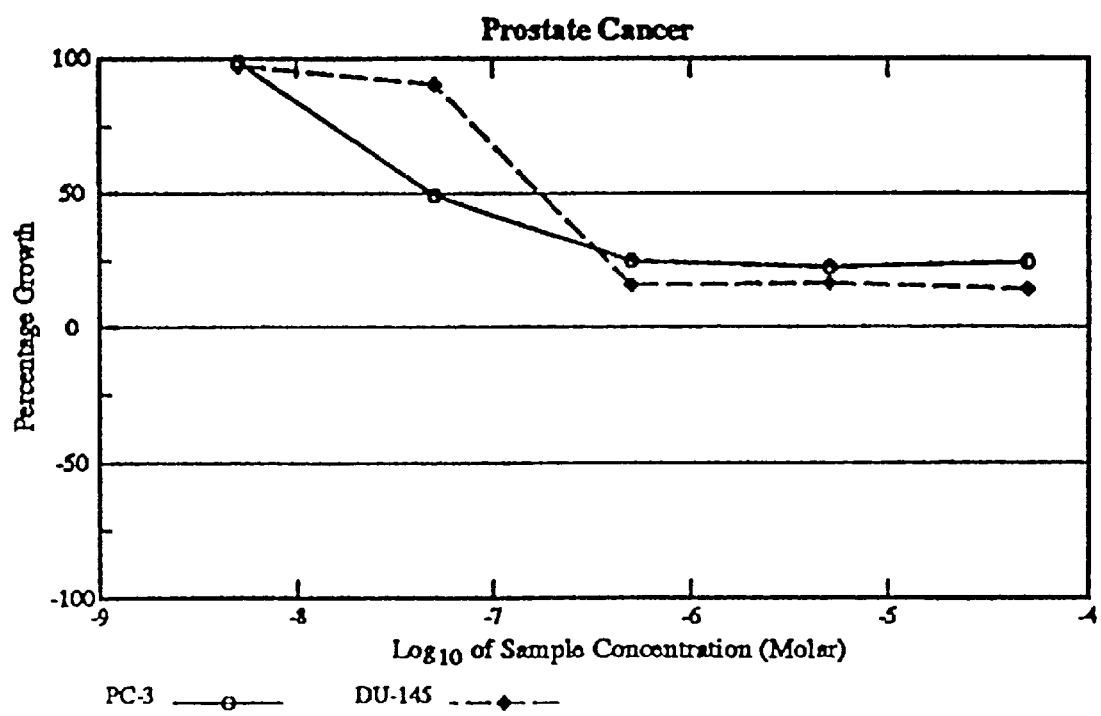
Figure 1I:
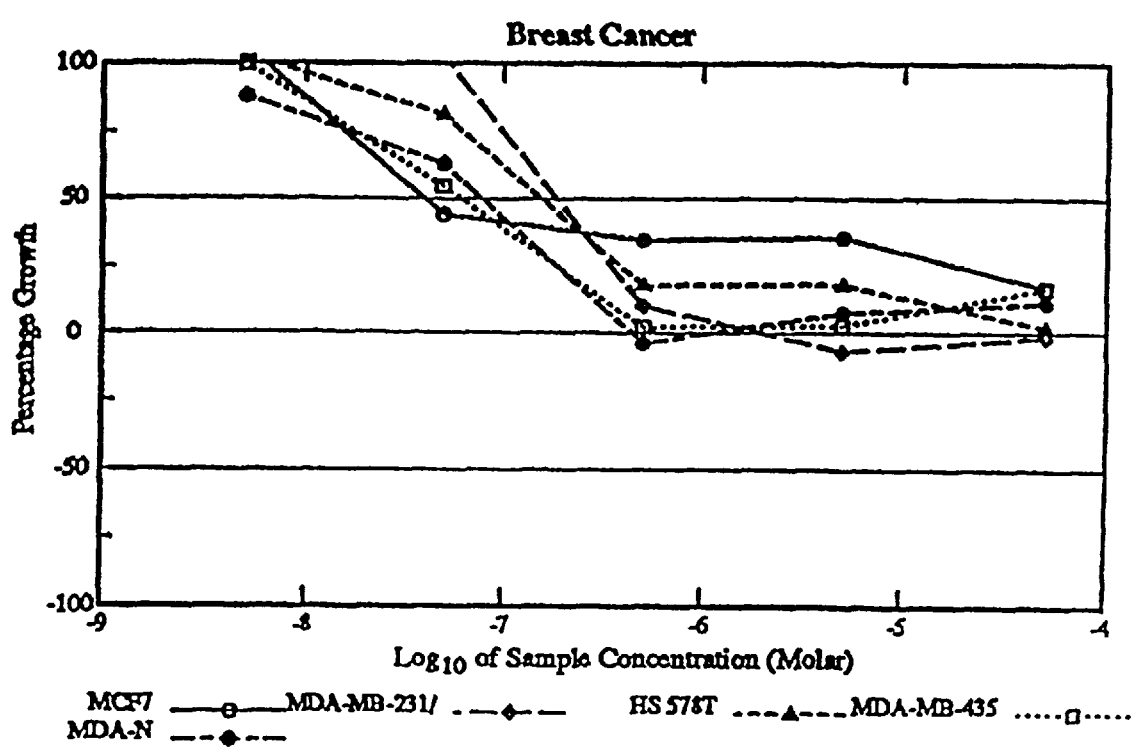

Strains of a marine blue-green alga (cyanobacterium), *Lyngbya majuscula*, were collected. From this algae, naturally occurring compounds, referred to as curacin A, curacin B, curacin C and curacin D, were isolated and purified. These compounds exhibited substantial biological activity, particularly antimitotic activity, in various tests conducted with such compounds.

The following paragraphs discuss isolating and purifying the novel naturally occurring compound curacin D. Novel, biologically active analogs of curacin A also are described. Curacin D and the semisynthetic analogs discussed below, including curazole, are collectively referred to herein as "curacin A analogs." Data concerning the biological activity of such compounds also is provided.

I. Isolation and Purification of the Curacins

Curacin A, B and C (Formulas 1–3, respectively), have been isolated and purified previously. The generally accepted numbering system for the curacin A analogs is provided in Formula 1.

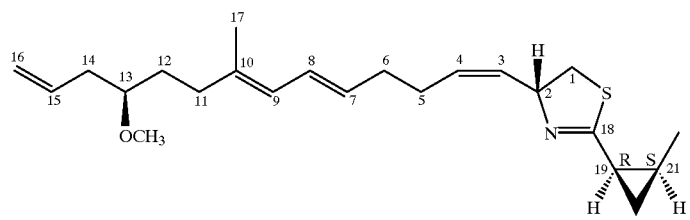

Formula 1-Curacin A

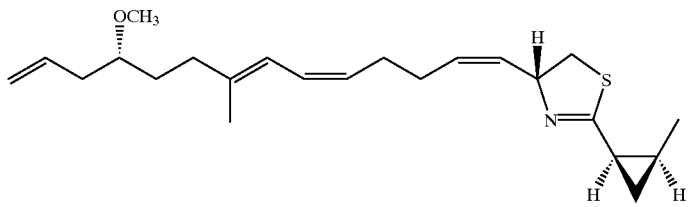

Formula 2-Curacin B

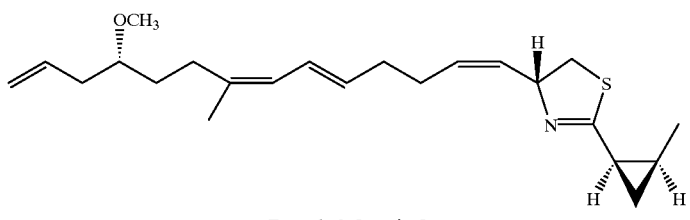

Formula 3-Curacin C

Curacin D, shown below as Formula 4, was isolated from a strain of *Lyngbya majuscula* obtained at St. Thomas, United States Virgin Islands.

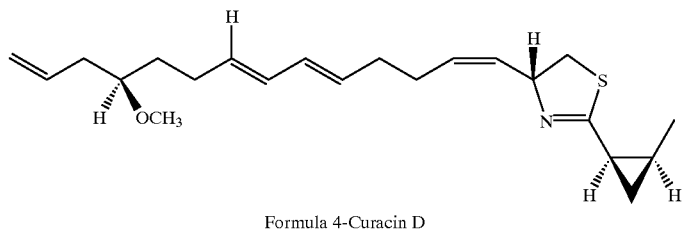

Formula 4-Curacin D

A. Isolation and Purification of Naturally Occurring Curacin Compounds

For details concerning the isolation and purification of curacins A and B see U.S. Pat. No. 5,324,739 to Gerwick, cited above. For information concerning the isolation and purification of curacin C, see Gerwick et al.'s "Curacins B and C, New Antimitotic Natural Products from the Marine Cyanobacterium *Lyngbya majuscula*, J. Nat. Prod., 58:1961–1965 (1995), which is incorporated herein by reference.

The isolation and purification of curacin D was accomplished as follows. The alga *Lyngbya majuscula* was harvested at Thomas, U.S. Virgin Islands, at a depth of from about 0.3 meters–2.0 meters. The alga was preserved in 90-percent isopropyl alcohol and transported to the U.S. In the laboratory, the alga was subjected to three methylene chloride-methanol extractions to isolate lipophilic compounds and an aqueous methanol extraction to isolate hydrophilic compounds. Each methylene chloride-methanol extraction was performed by washing algal tissue in 2:1 methylene chloride:methanol and collecting the supernatant liquid. The aqueous methanol extraction was performed by washing algal tissue in a 75% solution of methanol in water and collecting the supernatant liquid. The methylene chloride-methanol extract exhibited substantial toxicity in a brine-shrimp assay, with an $LD_{50}$ of about 10 µg/ml (a method for assaying extracts with brine-shrimp is provided by Example 1 of Gerwick's U.S. Pat. No. 5,324,739). The brine-shrimp assay was used as needed to evaluate the results of procedures used to purify the compound.

The alga were extracted using methylene chloride-methanol to yield a "crude" extract weighing more than a gram. 800 milligrams of the crude extract were subjected to two separate stages of vacuum chromatography. In the first stage, the extract was eluted using increasingly greater concentrations (5–100% in 5-percent increments) of ethyl acetate in hexane. The nonpolar fractions were collected.

The second stage of vacuum chromatography was performed on the second fraction collected in the first stage. Elution in the second stage was performed within a much smaller range of increasingly greater amounts of ethyl acetate in hexane (1 to 5% in 0.5 to 1.0% increments), and nonpolar fractions were collected.

The nonpolar fractions collected as discussed above were analyzed for brine-shrimp toxicity according to the method described in Example 1 of Gerwick's U.S. Pat. No. 5,324,739. Fractions showing substantial brine shrimp activity were pooled.

The pooled, brine-shrimp active nonpolar fractions were then subjected to normal-phase HPLC using 15% hexane/ethyl acetate. Curacin D was among the compounds isolated and purified by HPLC.

II. Curacin A Analogs Having a Thiazoline Ring

A number of curacin A analogs were made. Examples of novel, biologically active curacin A analogs synthesized to date having a thiazoline ring structure are shown below as Formulas 5–10.

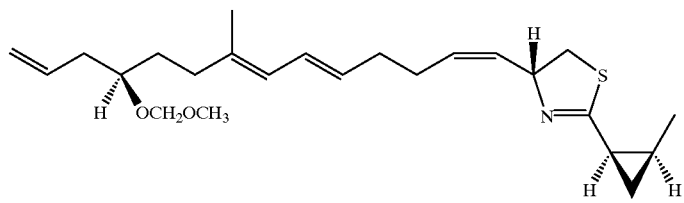

Formula 5-C13 Methylmethoxy

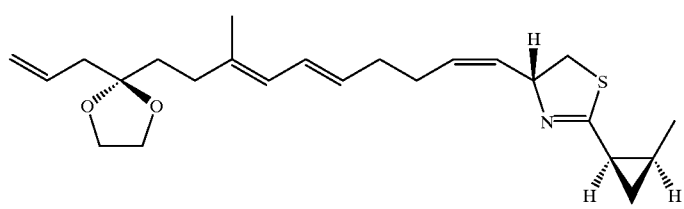

Formula 6-C13 Ethylenedioxy

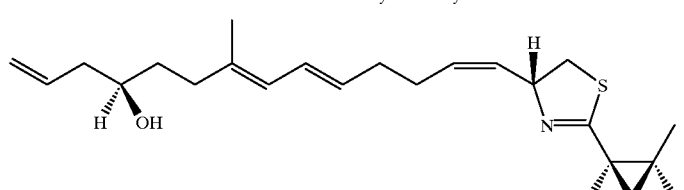

Formula 7-C13 Hydroxyl

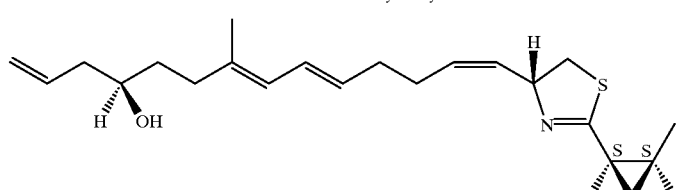

Formula 8-C13 Hydroxyl, Epi C19

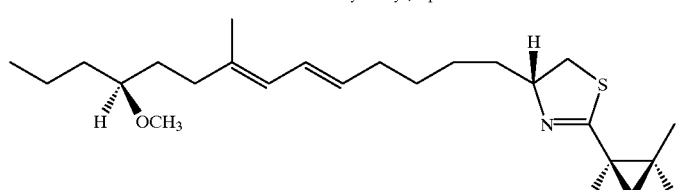

Formula 9-3,4,15,16-Tetrahydro

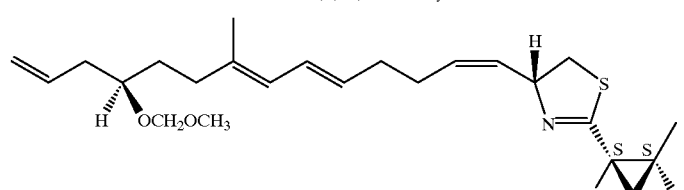

Formula 10-Methylmethoxy, Epi C19

Short identifiers also are provided adjacent the formula numbers for the compounds of Formulas 5–10. With respect to Formula 8, "epi" indicates that C19 is epimeric at that position with respect to the stereochemistry of curacin A. Curacin D and the curacin A analogs listed above can be generically represented by Formula 11.

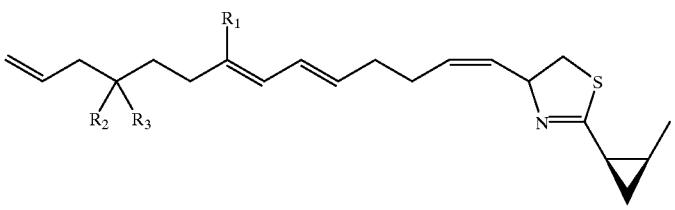

Formula 11-Generic Formula
for Curacin A Analogs Having a Thiazoline Ring $R_1$ is selected from the group consisting of hydrogen and "lower" aliphatic, particularly lower alkyl, chains. As used herein, the term "lower" when used in reference to chain length, such as alkyl and alkoxy chains, refers to chains having from about 1 to about 10 carbon atoms in the chain, and preferably from about 1 to about 5 carbon atoms in the chain. If $R_1$ is hydrogen, then $R_2$ and $R_3$ are independently selected from the group consisting of hydrogen, hydroxyl, lower alkyl, and lower alkoxy. If $R_1$ is lower alkyl, then $R_2$ and $R_3$ are selected from the group consisting of hydrogen, hydroxyl, and methylmethoxy. Furthermore, $R_2$ and $R_3$ can be bonded together to form ring structures, particularly five and six membered rings. See, Formula 6 above.

In Formula 11, stereochemistry is intentionally not illustrated. This is not to ignore stereochemistry, but rather to indicate that all stereoisomers are encompassed by the formula. In other words, the present invention is directed to all compounds having the structure of Formula 11, and all stereoisomers thereof. This is true of all generic formulas provided herein, i.e., all such structures also include all stereoisomers of the compounds illustrated, unless specifically noted otherwise.

The curacin A analogs discussed above were made either by total synthesis or semisynthetically, i.e., by modifying naturally occurring curacin A–D compounds, particularly curacin A, using classic organic synthetic techniques. Additional details concerning the synthesis of certain representative novel curacin A analogs are provided below in Examples 1–2.

The present curacin A analogs can be made via total synthesis techniques, or alternatively first by synthesizing curacin A and then making the analogs using classic organic synthetic techniques. A number of total syntheses of curacin A are known, including: J. D. White et al., "Synthesis of Curacin A: A Powerful Antimitotic from the Cyanobacterium *Lyngbya majuscula*," *J. Am. Chem. Soc.*, 117:5612–5613; J. D. White et al., "Absolute Configuration and Total Synthesis of (+)-Curacin A, an Antiproliferative Agent from the Cyanobacterium *Lyngbya majuscula*," *J. Am. Chem. Soc.*, 119:103–111 (1997); and Ito et al., "Enantioselective Synthesis of Curacin A. 2. Total Synthesis of Curacin A by Condensation of C1–C7, C8–C17, and C18–C22 Segments," *Tetrahedron Lett.*, 37:1799–1800 (1996). Each of these references is incorporated herein by reference. The synthetic methods described in these references can be used for the total synthesis of curacin A, which then can be converted to the curacin A analogs.

III. Curazole

As stated above, curacin A has demonstrated limited stability, particularly when stored neat, and perhaps in vivo. Curacin A stored neat has less biological activity than curacin A stored under a solvent. One possible reason for this is that curacin A, and likely curacins B–D as well, are readily air oxidized. A likely position for such oxidation to occur is at the sulfur atom of the thiazoline ring structure.

Curazole, shown below as Formula 12, has been synthesized and should be more resistant to oxidation.

Formula 12

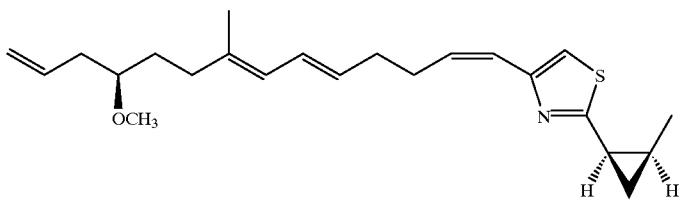

One reason for this is that the thiazoline ring characteristic of curacins A–D is converted to an aromatic thiazole (see, Formula 13) to form curazole, where the C1,2-double bond and lone pair electrons of sulfur contribute to the aromaticity of the thiazole ring structure. As a result, sulfur is less susceptible to oxidation, particularly by electrophilic oxidizing agents.

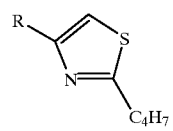

The $C_4H_7$ substituent attached to the thiazole ring structure can be any aliphatic group having three carbon atoms and 7 hydrogen atoms. Particular examples of the $C_4H_7$ group (also referred to as an "alkyl radical") include, without limitation, 1-butene (as illustrated group y Formula 14) or a cyclopropyl ring characteristic of the curacin A–D compounds (as illustrated by Formula 15).

Formula 14

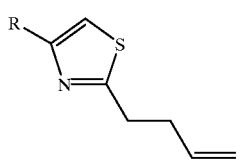

Formula 15

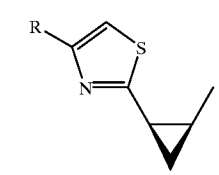

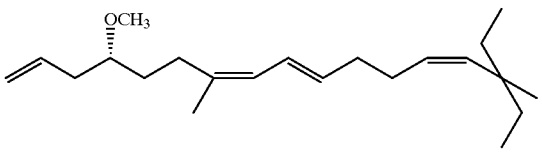

Formula 20-Curacin C Side Chain

R of Formula 13 generally is selected from the group consisting of aliphatic carbon chains having about 14 carbon atoms in the chain. Preferred aliphatic chains include at least one double bond, preferably at least 2 double bonds, and even more preferably 3 or more double bonds, wherein two of the double bonds are conjugated. Examples of aliphatic groups that satisfy these criteria, without limitation, are set forth below as Formulas 16–23, where the thiazole ring is bonded to the carbon atom at the right-most end of each formula.

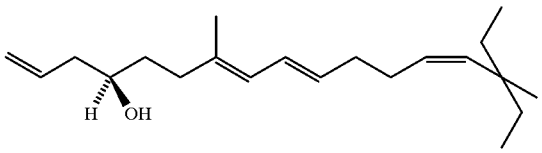

Formula 21-C13 Hydroxyl

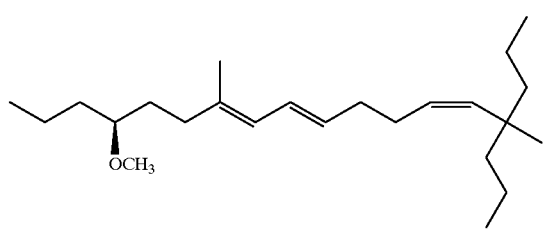

Formula 16-C15,16-Dihydro

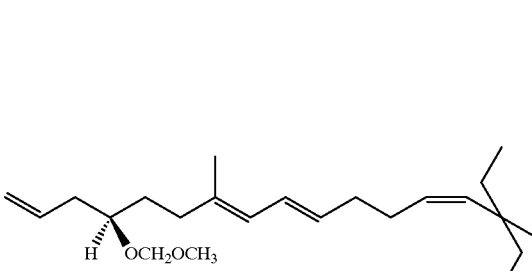

Formula 22-C13 Methyl Methoxy

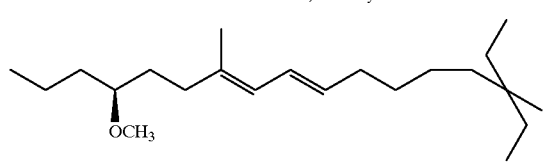

Formula 17-C3,4,15,16-Tetrahydro

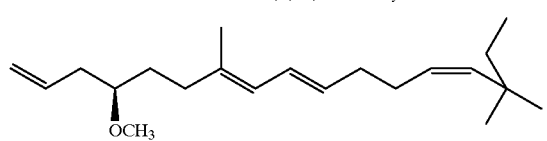

Formula 18-C13 Methoxy

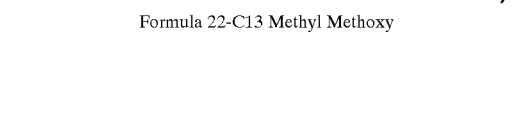

Formula 23-Ethylenedioxy

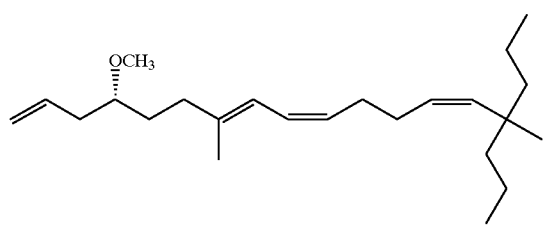

Formula 19-Curacin B Side Chain

Curazole and other curacin A analogs having the thiazole ring can be represented by generic Formula 24.

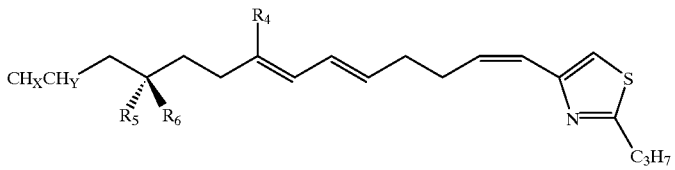

Formula 24-Generic Formula for Curazole
And Curacin A Analogues having a Thiazole Ring wherein $R_4$ is hydrogen or lower alkyl; and $R_5$ and $R_6$ are independently hydrogen, hydroxyl, lower alkyl, or lower alkoxy, or $R_5$ and $R_6$ are bonded together to form a ring structure having from three to six atoms in the ring. X is 2 or 3 and Y is 1 or 2. The X and Y designations indicate a terminal bond, i.e., a double bond between C15 and C16, or that C16 can be a methyl group and C15 a methylene group. Thus, for a terminal double bond, X=2 and Y=1. For a C16 methyl group, X=3 and Y=2. Moreover, the $C_4H_7$ substituent can be either a butene, such as 1-butene, or can be a cyclopropyl ring having at least one methyl group bonded thereto.

IV. Biological Activity of Curacin A Analogs

The curacin A analogs described above have been found to be antiproliferative compounds against living cells, and likely are antimitotic agents which act by interfering with cellular mechanisms of tubulin formation. Tests performed using nearly sixty different cancer cell lines (see Examples 4–123 below) indicate that the cytotoxic profile of the curacins, curazole and its analogs, and stereoisomers thereof, share certain similarities with other antimitotic agents, such as the Vinca alkaloids and taxol, that are useful as antineoplastics. Thus, it would be within the purview of persons skilled in the art of preparing pharmaceutical formulations to add such compounds to pharmaceutical inert carriers, excipients, etc. suitable for administration to a subject, in a manner similar to that used for preparing such formulations of conventional antimitotic compounds.

The effectiveness of curacin A and stereoisomers thereof for reducing a population of representative arthropods (for brine shrimp example; see Example 1 of Gerwick's U.S. Pat. No. 5,324,739) indicate that the compounds described above have general utility as agents for reducing populations of arthropods such as insects.

The Examples set forth below also indicate that such compounds have substantial antiproliferative activity against living cells in culture.

Tests involving administration of curacin A-containing formulations to mice (data not shown) indicate that the curacins are bioavailable and effective in vivo against proliferating cells when administered by various direct methods and when administered orally. These results are consistent with similar attributes of conventional antimitotic agents. In addition, these tests indicate that curacin A and curacin A analogs can be administered to animal subjects using dosage protocols that are substantially similar to such protocols used with other antimitotics.

Ex vivo experiments involving the administration of curacin-containing formulations to mice (1–10 mg/kg) indicate that the curacins exhibit substantial effect against spleen lymphocytes.

The results and data set forth in this disclosure indicate that curacins A–D and curacin A analogs are more active against proliferating cells than against quiescent cells.

Consistent with the herbicidal activity of conventional antimitotic compounds, the curacins would be expected to also exhibit herbicidal properties.

V. EXAMPLES

The following examples are provided solely to illustrate certain features of the invention. These examples should not be construed to limit the invention to the particular features described.

A. Experimental Procedures

1. Materials

Electrophoretically homogeneous bovine brain tubulin was prepared as described previously (20). Nonradiolabeled colchicine was obtained from Sigma and [$^3$H]colchicine from Dupont-NEN. Stock 2.0 M solutions of monosodium glutamate were adjusted to pH 6.6 with HCl. MCF-7 breast cancer cells were obtained from Dr. D. Scudiero, National Cancer Institute. Curacin A is referred to in the tables provided below, and was obtained as stated in Gerwick's U.S. Pat. No. 5,324,739. All data presented for curacin A represent averages obtained in contemporaneous experiments with natural and synthetic drug. All drugs were dissolved in dimethyl sulfoxide, and control reaction mixtures contained an equivalent amount of the solvent.

2. Methods

NMR spectra were recorded on Bruker AM 400 and AC 300 spectrometers. Chemical shifts were referenced to the solvent $C_6D_6$ signals at 7.2 ppm for $^1$H NMR and at 128 ppm for $^{13}$C NMR. Mass spectra were recorded on Kratos MS 50 TC and Finnigan 4023 mass spectrometers. Gas chromatography/mass spectrometry was carried out utilizing a Hewlett-Packard 5890 Series II gas chromatograph connected to a Hewlett-Packard 5971 mass selective detector. UV and IR spectra were obtained, respectively, on Hewlett-Packard 8452A and Nicolet 510 spectrophotometers.

B. Working Examples

Example 1

This example describes the synthesis of 3,4,15,16-tetrahydrocuracin A. [$(C_6H_5)_3$P]$_3$RhCl (11.3 mg, 12.2 μmol) in 0.50 mL $CH_2Cl_2$ was added to curacin A (49 mg, 131 μmol) in 0.50 mL ethanol. An additional 2.5 mL of $CH_2Cl_2$ was added, and the reaction flask, with an attached balloon, was charged with $H_2$. After 7 hours at room temperature, 40 mL of a 1:1 mixture of ethanol and diethyl ether was added to the reaction mixture, and the catalyst was removed by filtration through a silica plug. Pure 3,4,15,16-tetrahydrocuracin A was obtained from the filtrate by HPLC on a Phenomenex Maxsil 10 μm silica column (50×1.0 cm) using 4% (v/v) ethyl acetate in hexanes (eluted at 680–730 mL).

The chemical characterization of compound 3,4,15,16-tetrahydrocuracin A is as follows: $^1$H NMR ($C_6D_6$, 300 MHz) δ6.40 (dd, 1H, J=14.9, 11.1, H-8), 6.01 (d, 1H, J=11, H-9), 5.65 (m, 1H, H-7), 4.15 (m, 1H, H-2), 3.18 (s, 3H, —OCH$_3$), 3.08 (m, 1H, H-13), 2.90 (dd, 1H, J=10.8, 8.3, H-1b), 2.60 (dd, 1H, J=10.2, 9.8, H-1a), 2.15 (m, 2H, H-11), 2.13 (m, 2H, H-6), 1.70 (s, 3H, H-17), 1.69–1.51 (m, 3H, H-12 and H-19), 1.5–1.3 (m, 10H, H-3, H-4, H-5, H-14, and H-15), 1.2 (m, 1H, H-20b), 1.18 (d, 3H, J=6.3, H-22), 0.95 (m, 1H, H-21), 0.9 (m, 3H, H-16), 0.75 (m, 1H, H-20a);

GC EIMS (% rel. ins.) obs. $[M]^+$ m/z 377 (65), 362 $[M-CH_3]^+$ (36), 346 $[M-OCH_3]^+$ (29), 334 $[M-C_3H_7]^+$ (11), 302 (11), 290 $[M-C_5H_{11}O]^+$ (33), 276 $[M-C_6H_{13}O]^+$ (83), 262 $[M-C_7H_{15}O]^+$ (15), 234 (18), 222 (13), 208 (29)' 194 (17), 182 $[C_{10}H_{16}NS]^+$ (17), 180 $[M-C_{13}H_{23}O]^+$ (16), 176 (33), 168 $[C_8H_{12}NS]^+$ (18), 166 (28), 154 $[C_8H_{12}NS]^+$ (33), 141 (60), 140 $[C_7H_{10}NS]^+$ (100), 113 (31), 107 (25), 105 (33), 99 $[C_5H_7S]^+$ (36), 93 (45), 91 (40), 87 $[C_5H_{11}O]^+$ (47), 81 (40), 79 (51), 67 $[C_5H_7]^+$ (28), 55 $[C_4H_7]^+$ (39).

Example 2

This example describes a method for making curazole, i.e., [13R,19R,21S]-1,2-didehydrocuracin A. $MnO_2$ (200 mg, 2.3 mmol) was added to 2.0 mL of hexanes containing curacin A (17.6 mg, 47 μmol). The reaction was stirred, and maintained at a temperature of about 25° C. Reaction progress was monitored by TLC. After 5 days the $MnO_2$ was removed by filtration and washed with hexanes. The wash was added to the filtrate and the solvent removed under vacuum. The residue was dissolved in 2% (v/v) ethyl acetate in hexanes. HPLC purification was on a Versapack 10 μm silica column (30×0.41 cm), developed at 2.0 mL/min with 2% (v/v) ethyl acetate in hexanes.

The chemical characterization of compound 10 (colorless oil, 5 mg, 13.5 μmol, 29% yield) is as follows: IR $v_{max}$ (film) 3017, 2924, 2851, 1640, 1617, 1505, 143 g, 1385, 1354, 1084, 964, 914, 779 cm$^{-1}$; UV $\lambda_{max}$ (ethanol) 224 nm (log ε, 4.43), 242 nm (log ε 4.49), 252 nm (log ε 4.42); $^1$H NMR ($C_6D_6$, 400 MHz) δ6.46 (s, 1H, H-1), 6.44 (bd, 1H, J=11.7, H-3), 6.40 (bdd, 1H, J=15.2, 10.9, H-8), 5.97 (bd, 1H, J=10.9, H-9), 5.83 (ddt, 1H, J=17.0, 10.2, 7.3, H-15), 5.68 (dt, 1H, J=11.7, 7.3, H-4), 5.66 (bd, 1H, J=15.2, H-7), 5.02 (m, 2H, H-16), 3.13 (s, 3H, —OCH3), 3.04 (tt, 1H, J=6.0, 6.0, H-13), 2.89 (bdt, 2H, J=7.4, 6.0, H-5), 2.30 (m, 2H, H-6), 2.19 (m, 2H, H-14), 2.13 (m, 2H, H-11), 2.00 (dt, 1H, J=8.1, 5.2, H-19), 1.67 (s, 3H, H-17), 1.60 (m, 2H, H-12), 1.13 (m, 1H, H-20b), 1.05 (d, 3H, J=6.0, H-22), 0.95 (m, 1H, H-21), 0.86 (ddd, 1H, J=8.1, 5.2, 4.3, H-20a);

$^{13}$C NMR ($C_6D_6$, 100 MHz) δ168.68 (C18), 153.88 (C2), 136.00 (C10), 135.58 (Cl5), 133.02 (C4), 131.97 (C7), 127.76 (C8), 125.73 (C9), 122.90 (C3), 116.72 (C16), 115.26 (C1), 79.99 (C13), 56.30 (—OCH3), 38.07 (C14), 35.78 (C11), 33.35 (C6), 32.15 (C12), 29.58 (C5), 19.85 (C19), 16.57 (C17), 16.47 (C21), 14.94 (C20), 12.66 (C22);

GC EIMS (% ref. int.) obs. $[M]^+$ m/z 371 (11), 356 $[M-CH_3]^+$ (29), 340 $[M-OCH_3]^+$ (26), 330 (18), 298 (21), 286 (36), 272 (37), 258 (11), 230 (11), 204 (24), 178 (81), 161 (30), 153 (50), 133 (17), 119 (76), 105 (53), 97 (100), 91 (51) 79 (64), 67 (35), 55 (25).

Example 3

The curacin A analog discussed herein and others were compared with curacin A as inhibitors of tubulin assembly and inhibitors of colchicine binding to tubulin. These compounds were also evaluated to determine their inhibitory effects on the growth of MCF breast cancer cells.

The binding of [$^3$H]colchicine to tubulin was measured by the DEAE-cellulose filter method as described by Kang et al., "N-acetylcolchinol O-methyl Ether and Thiocolchicine, Potent Analogs of Colchicine Modified in the C Ring: Evaluation of the Mechanistic Basis for Their Enhanced Biological Properties," *J. Biol. Chem.* 265:10255–1–259 (1990). Reaction mixtures contained 1.0 μM (0.1 mg/mL) tubulin, 1.0 M monosodium glutamate, 0.1 M glucose-1-phosphate, 1.0 mM $MgCl_2$, 1.0 mM GTP, 0.5 mg/mL bovine serum albumin, 5% (v/v) dimethyl sulfoxide, 5.0 μM [$^3$H] colchicine and inhibitor at either 5.0 or 50 μM as indicated. These reaction conditions were used because they strongly stabilize the colchicine binding activity of tubulin. The values presented represent averages of three experiments, each with duplicate samples.

Tubulin polymerization was followed turbidimetrically at 350 nm in Gilford model 250 spectrophotometers equipped with electronic temperature controllers. All concentrations refer to the final reaction volume of 0.25 mL, although the preincubation was performed in 0.24 mL, followed by addition of 10 μL of 10 mM GTP. Reaction mixtures contained 1.0 mg/mL tubulin, 0.8 M monosodium glutamate, 4% dimethyl sulfoxide and varying drug concentrations. Samples were preincubated for 15 minutes at 30° and chilled on ice. GTP was added to each reaction mixture, and these were placed in cuvettes held at 0°. Baselines were established, the temperature was raised to 30° (at a rate of about 0.5°/sec), and polymerization was followed for 20 minutes. $IC_{50}$ values were determined by graphical interpolation of experimental points, with drug-containing samples compared to control reaction mixtures containing dimethyl sulfoxide but no drug. At least three independent $IC_{50}$ values were obtained with each compound.

$IC_{50}$ values for inhibition of cell growth were obtained by measuring the amount of total cell protein with the sulforhodamine B assay as described by Skehan et al., "New Colorimetric Cytotoxicity Assay for Anticancer-drug Screening," *J. Natl. Cancer Inst.*, 82:1107–1112 (1990). MCF-7 cells were grown in RPMI 1640 medium containing 17% fetal calf serum, 12 μg/mL gentamicin sulfate and 2 mM glutamine at 37° in 5% $CO_2$. Confluent cells were trypsinized, diluted 40-fold, and seeded into 96-well microtiter plates. After 24 hours of growth without drug, medium with varying concentrations of drug was added to different wells (final concentration of dimethyl sulfoxide, 0.1%). $IC_{50}$ values were determined after an additional 48 hours. The values presented are averages from at least two independent experiments.

The results are presented below in Table 1. Table 1 demonstrates that the curacin A analogs are biologically active compounds. The $R_1$–$R_3$ substituents referred to in Table 1 are with reference to Formula 11, which, for convenience, is reproduced above Table 1.

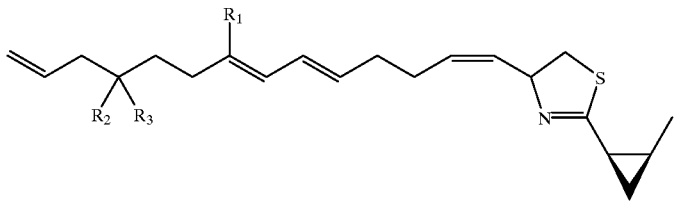

TABLE 1

| Compound | $R_1$ | $R_2$ | $R_3$ | Inhibition of Tubulin Polymerization $IC_{50} \pm SD(\mu M)$ | Inhibition of Colchicine Binding[a] % Inhibition ± SD | Inhibition of MCF-7 Growth $IC_{50} \pm SD(\mu M)$ |
|---|---|---|---|---|---|---|
| Curacin A | | | | 0.72 ± 0.2 | 94 ± 2 | 0.038 ± 0.01 |
| Curacin D | H | H | —OCH₃ | 4.8 ± 0.4 | 53 ± 10 | 0.34 ± 0.1 |
| C15,16-dihydro | | | | 1.2 ± 0.2 | 85 ± 7 | 0.046 ± 0.01 |
| C3,4,15,16 Tetrahydro | | | | 4.6 ± 1 | 1 ± 1(28 ± 6) | 3.3 ± 2 |
| Curazole | | | | 0.74 ± 0.01 | 74 ± 11 | 0.30 ± 0.07 |
| 1-butene derivative (i.e., cyclopropyl ring opened). | | | | 0.92 ± 0.2 | 83 ± 6 | 0.30 ± 0.2 |
| C13 Hydroxyl, Epi C19 | | | | 0.73 ± 0.1 | 71 ± 5 | 0.61 ± 0.2 |
| C13 Methyl-methoxy, Epi C19 | | | | 3.2 ± 0.3 | 16 ± 3(32 ± 4) | 3.1 ± 2 |
| C13 Hydroxyl | CH₃ | H | —OH | 0.87 ± 0.09 | 82 ± 7 | 0.45 ± 0.02 |
| C13 Methyl-methoxy | CH₃ | H | —OCH₂OCH₃ | 0.64 ± 0.2 | 81 ± 6 | 0.22 ± 0.02 |
| C13 Ethylene-dioxy | CH₃ | —OCH₂CH₂O— | | 0.78 ± 0.3 | 92 ± 1 | 0.030 ± 0.01 |

[a]Inhibitor concentration 5.0 $\mu$M, except for the values in parentheses, where the inhibitor concentration was 50 $\mu$M.

Examples 4–63

In these examples, curazole was subjected to the drug screening procedure employed by the National Cancer Institute for the screening of drugs having possible anticancer utility. The screening procedure employed a diverse, disease-oriented panel consisting of 60 different human tumor cell lines organized into seven disease-specific subpanels. Curazole was tested over a wide range of concentrations for cytotoxic or growth-inhibitory effects against each cell line comprising the panel. The seven subpanels represented diverse histologies (leukemias, melanomas, and tumors of the lung, colon, kidney, ovary, and brain).

Curazole was tested over a period of several days. During this period the cells were continuously exposed to five $\log_{10}$-spaced concentrations of the drug starting at about $10^{-4}$ $\mu$g/mL. The tests produced 60 individual dose-response curves, one for each cell line (i.e., one for each example).

The data are disclosed in FIGS. 1A–1I as dose-response curves. The data of FIGS. 1A–1I are summarized using a mean-graph format, as shown in FIG. 2.

Figure 2:
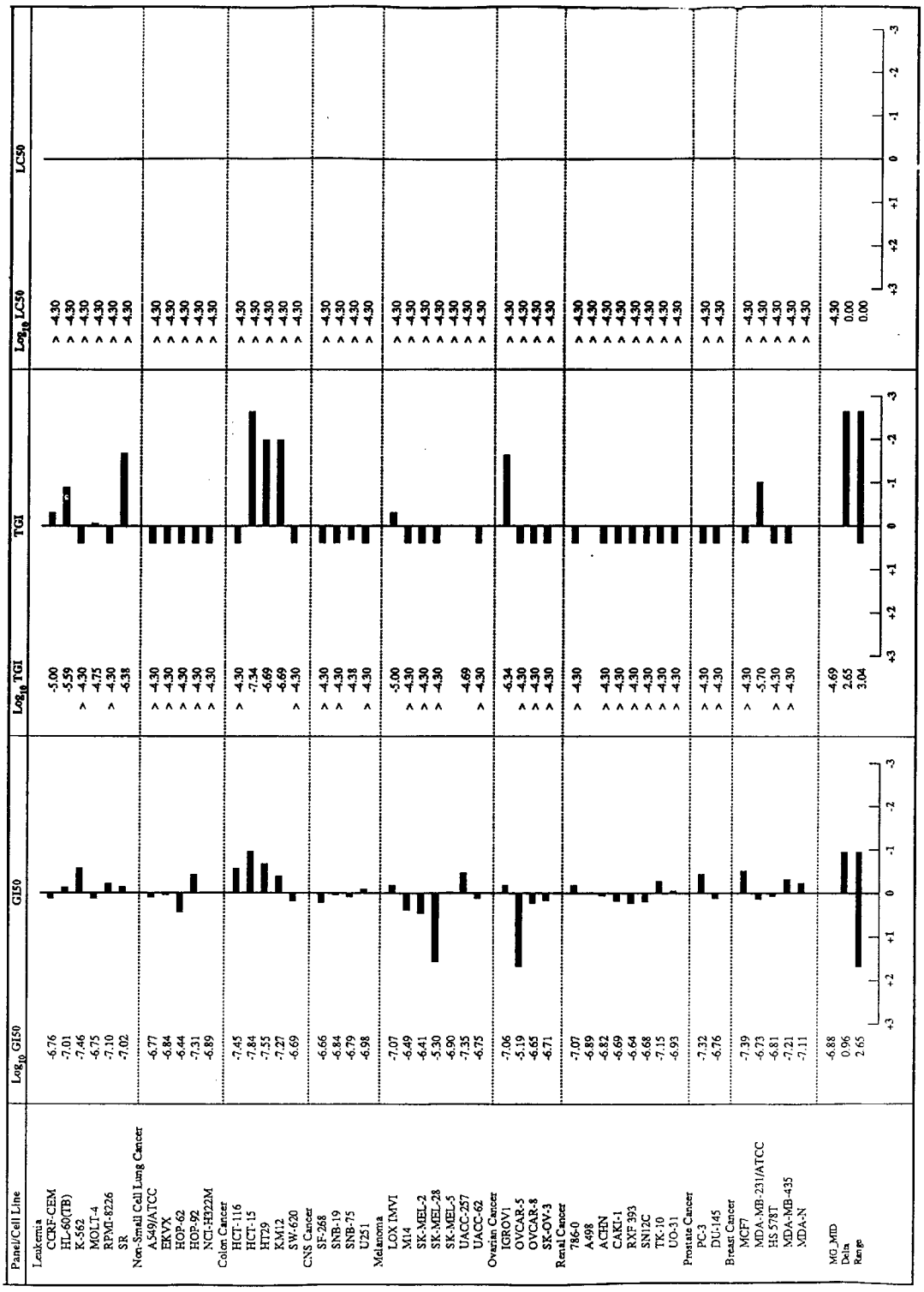
FIG. 2 shows mean plots of data from FIGS. 1A–1I, wherein the left-hand and mean plot is of $GI_{50}$ data, the middle mean plot is of TGI data, and the right-hand mean plot is of $LC_{50}$ data.
Figure 3A:
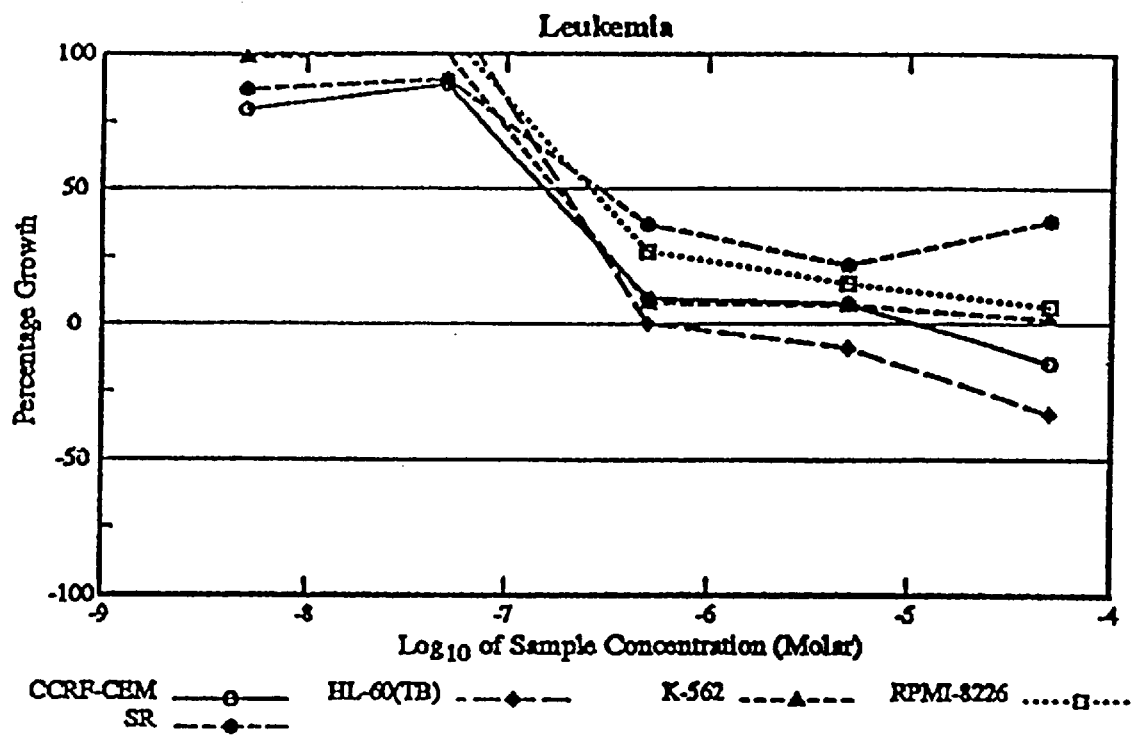
Figure 3B:
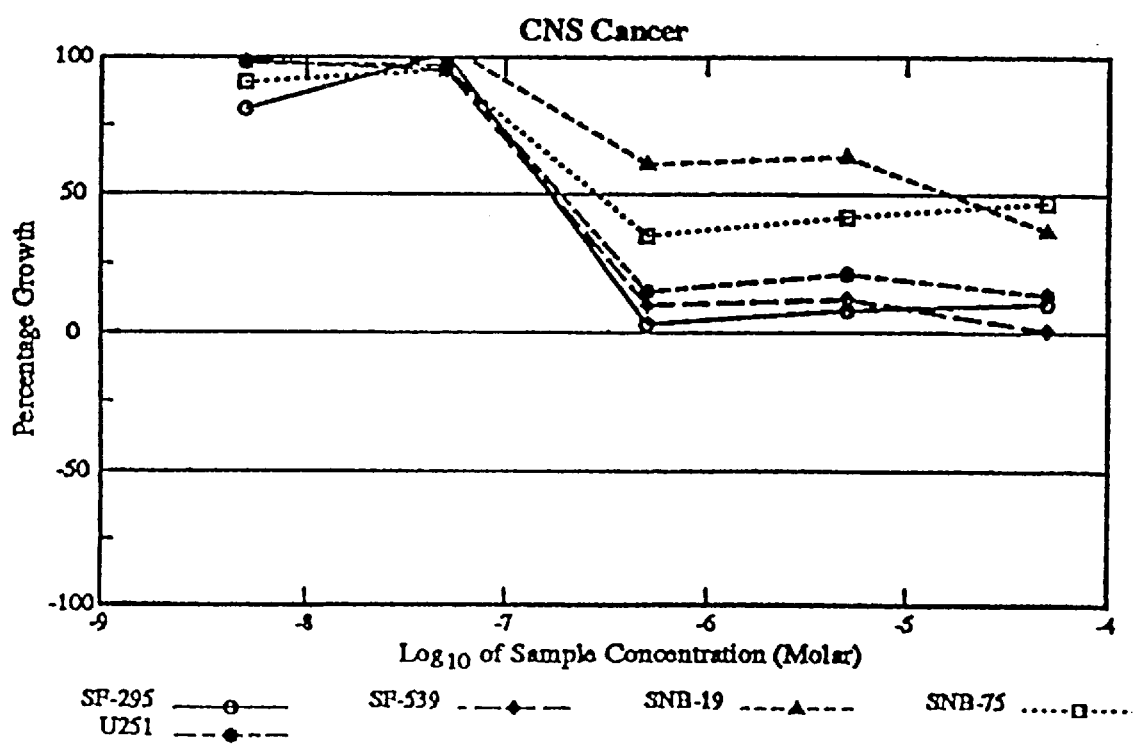
Figure 3C:
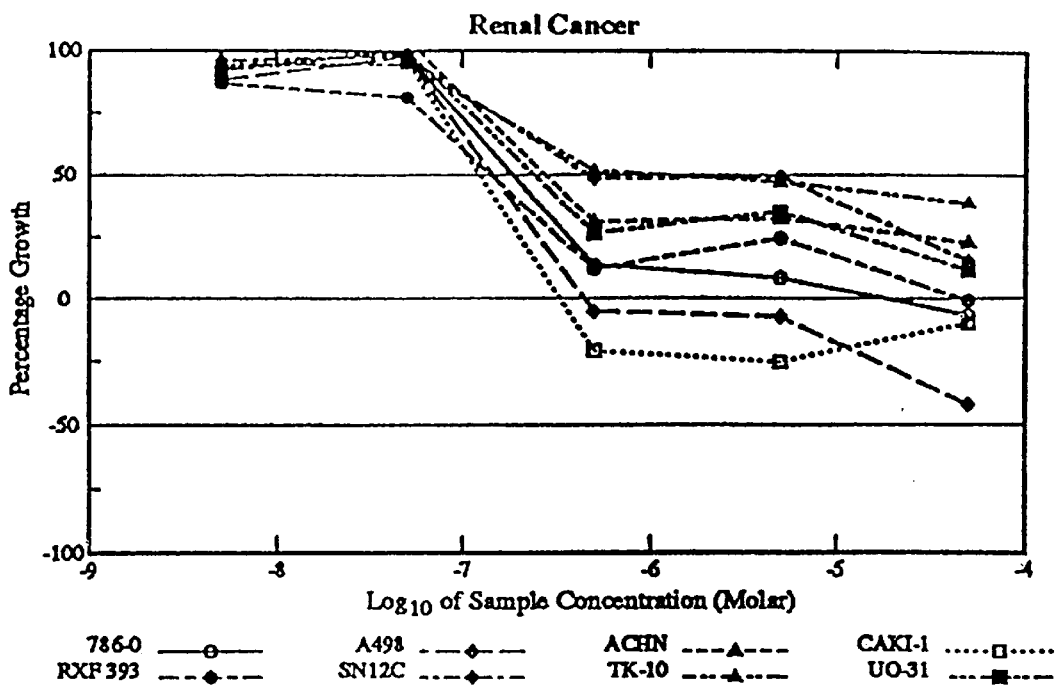
Figure 3D:
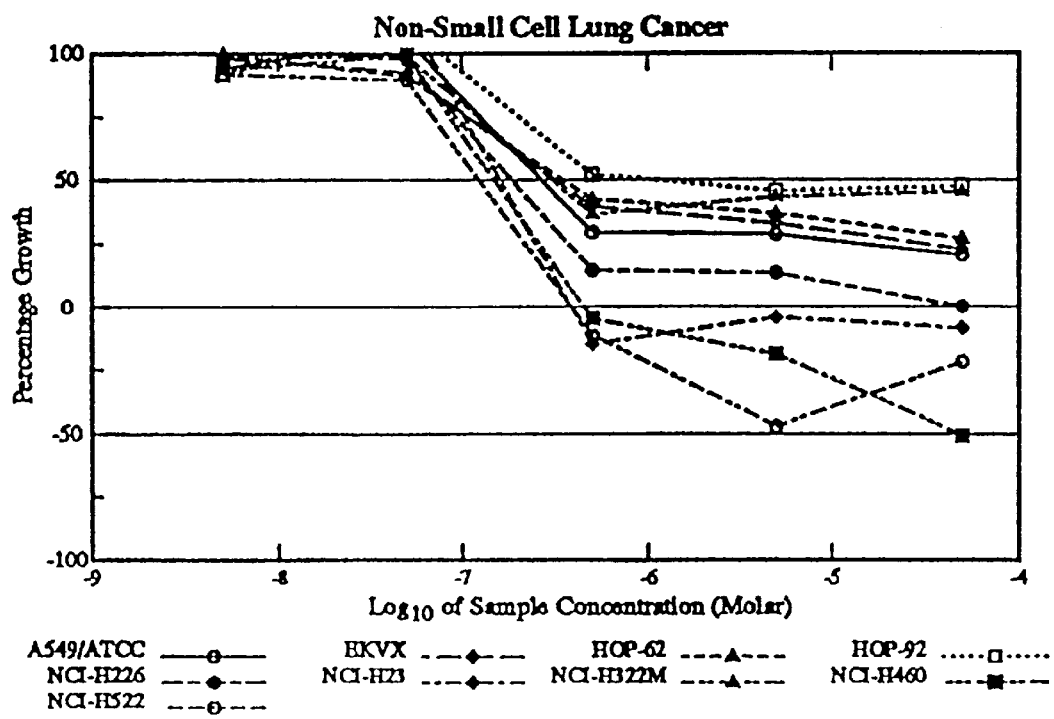
Figure 3E:
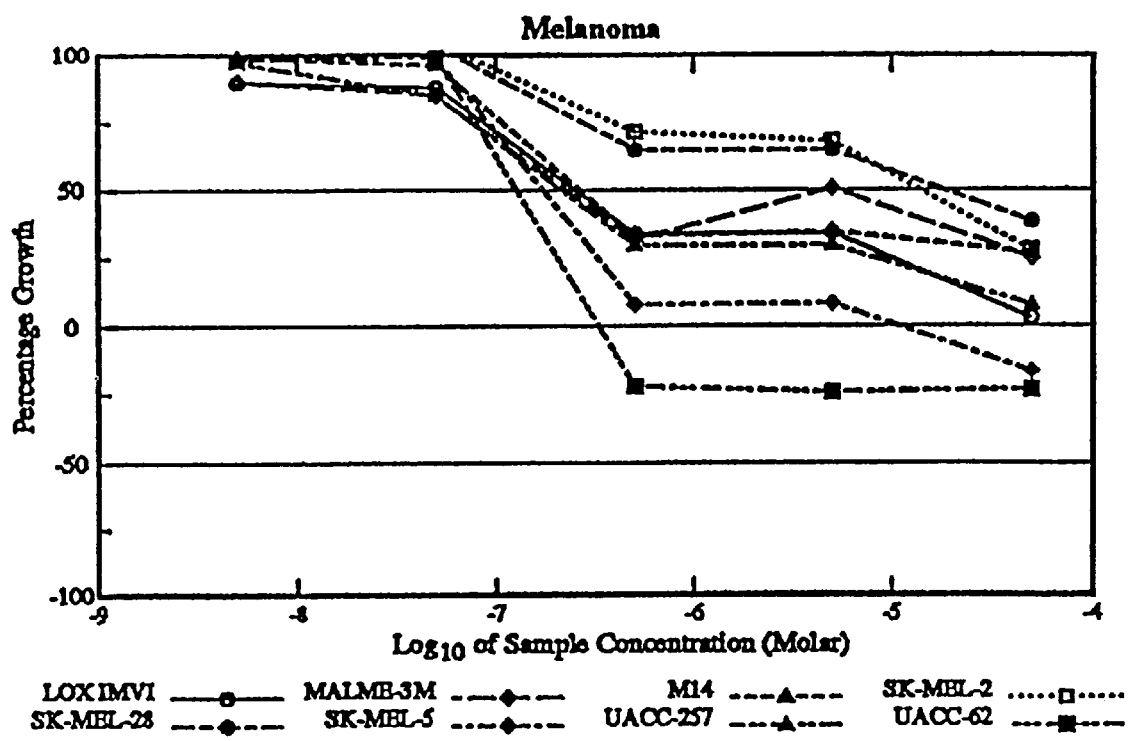
Figure 3F:
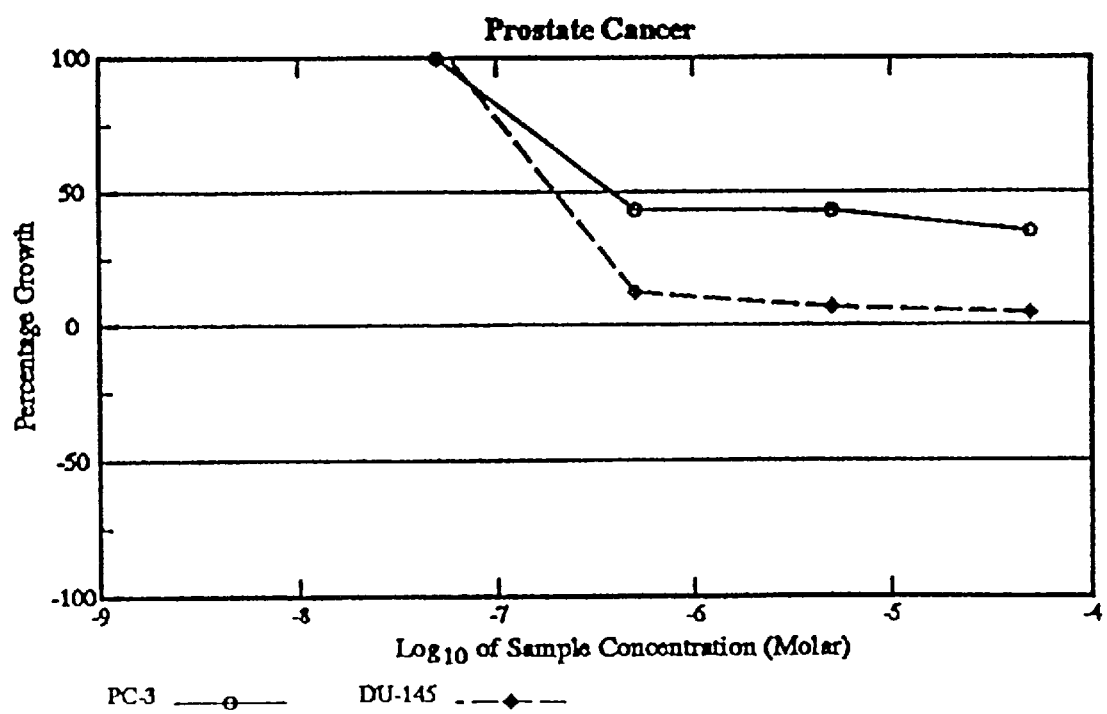
Figure 3G:
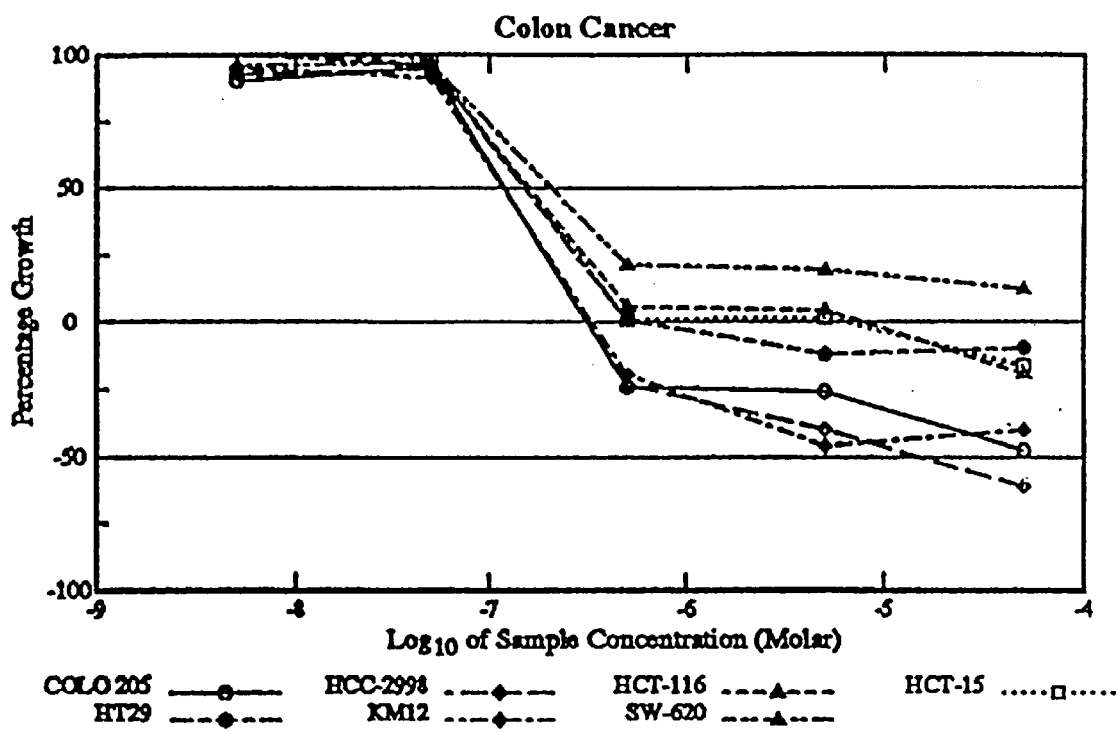
Figure 3H:
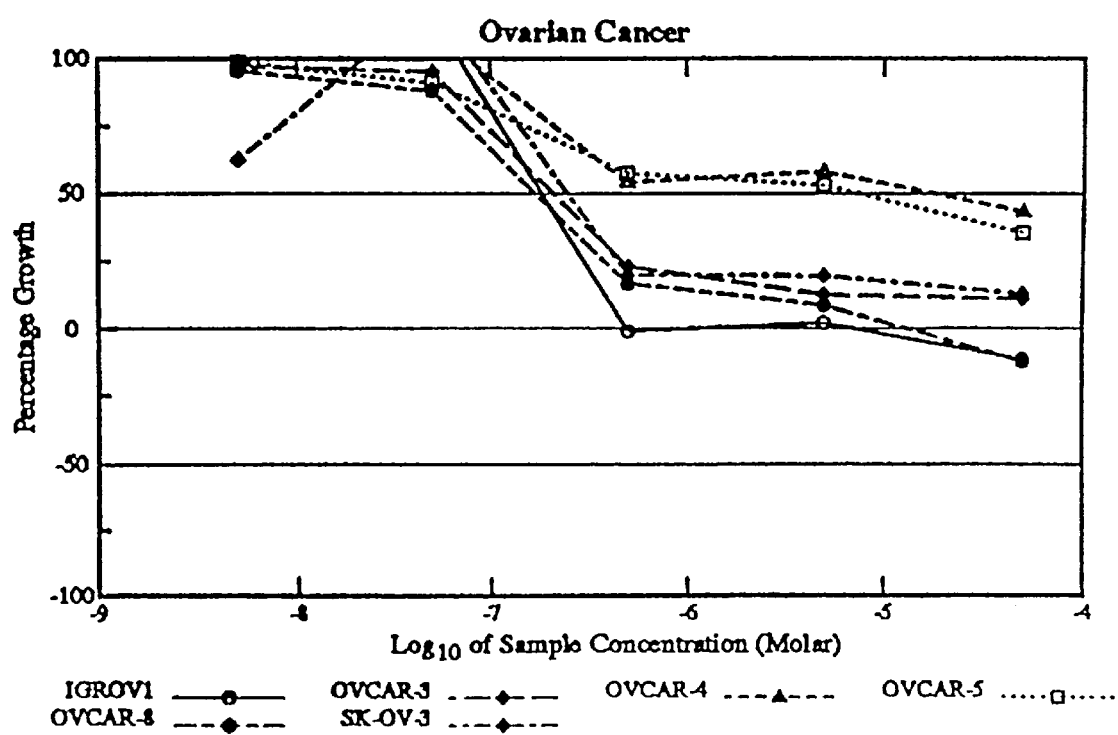
Figure 31:
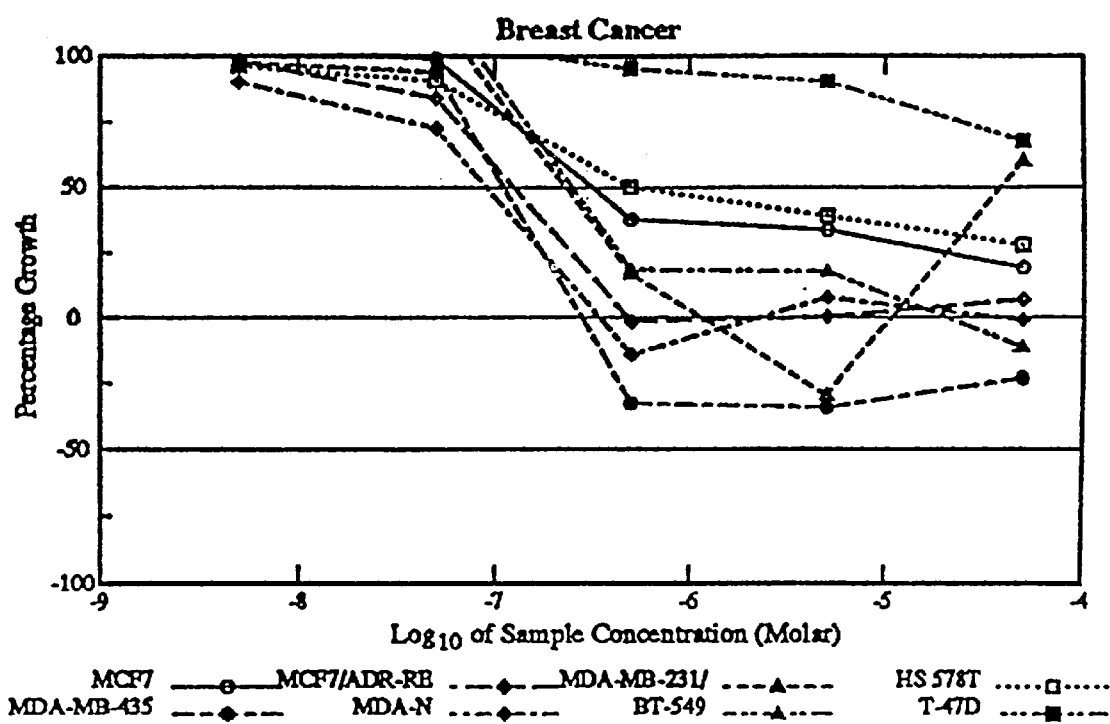

To produce data for the mean-graph format shown in FIG. 2, a concentration of the extract that produced a target level response was calculated for each cell line. Three different response parameters were evaluated. The first response parameter was the growth inhibition ("$GI_{50}$"), which is the concentration of curazole that produced an apparent 50% decrease in the number of tumor cells relative to the appropriate control (not exposed to curazole) at the end of the incubation period. The second response parameter was the total growth inhibition ("TGI"), which is the concentration at which the number of tumor cells remaining at the end of the incubation period substantially equaled the number of tumor cells existing at the start of the incubation period. The third response parameter was the lethal concentration ("$LC_{50}$"), which is the concentration of curazole that caused an apparent 50 percent reduction in the number of tumor cells relative to the appropriate control (not exposed to curazole) at the start of the incubation period.

In a typical $GI_{50}$ mean graph (e.g., left graph of FIG. 2), the relative position of the vertical reference line along the horizontal concentration axis is obtained by averaging the negative $\log_{10}GI_{50}$ values for all the cell lines tested against the extract. Horizontal bars are then plotted for the individual negative $\log_{10}GI_{50}$ values of each cell line relative to the vertical reference line. The $GI_{50}$ graph thus provides a characteristic fingerprint for the extract, displaying the individual cell lines that are proportionately more sensitive than average (bars extending to the right of the reference line) or proportionately less sensitive than average (bars extending to the left of the reference line). The length of a bar is proportional to the difference between the $\log_{10}GI_{50}$ value obtained with the particular cell line and the mean (represented by the vertical reference line). For example, for a given cell line, a bar extendual c cellular responses to the extract.

Similar mean graphs are shown in FIG. 2 for the TGI (middle graph) and $LC_{50}$ (right-hand graph) response parameters.

A computer program called COMPARE is used by the National Cancer Institute to explore similarities and differences in the mean graph fingerprint of the sample drug compared to mean graph fingerprints of compounds in the standard agent database. COMPARE is used to rank the similarity of the mean graph profile of the sample extract or drug to the patterns of all the other compounds in the NCI screening database or a defined subset thereof.

The data of these Examples 4–63 were subjected to COMPARE analysis and the results are presented below in Tables 2–4.

TABLE 2

COMPARE CORR G150
PARENT - NSC S 695032 LCONC = −4.30 M (BV)
PEARSON

|   | NSC | LCONC | (MAX X) | CORR COEFF. | (N) | CHEM. NAME |
|---|---|---|---|---|---|---|
| 1 | 153858 | −4.00 | 15 | 0.514 | 46 | Maytansine |
| 2 | 67574 | −3.00 | 61 | 0.513 | 46 | Vinchristine Sulfate |
| 3 | 332598 | −9.00 | 9 | 0.472 | 46 | Rhizoxin |
| 4 | 368390 | −2.30 | 13 | 0.454 | 46 | DUP785 (Brequinar) |
| 5 | 126771 | −3.60 | 15 | 0.442 | 46 | Dichloroally Lawsone |
| 6 | 208734 | −3.65 | 15 | 0.417 | 46 | Aclacinomycin A |
| 7 | 366140 | −3.20 | 15 | 0.407 | 46 | Pyrazoloacridine |
| 8 | 366241 | −4.00 | 7 | 0.392 | 34 | Bis-Pyridocarbazolium DMS |
| 9 | 284751 | −3.52 | 15 | 0.387 | 46 | 8-CL CYC AMP |
| 10 | 143095 | −2.30 | 12 | 0.382 | 46 | Pyrazofurin |
| 11 | 126849 | −2.60 | 15 | 0.366 | 46 | 3-Deazauridine |

TABLE 3

COMPARE CORR TGI
PARENT = NSC S 695032 LCONC = −4.30 M (BV)
PEARSON

|   | NSC | LCONC | (MAX X) | CORR. COEFF. | (N) | CHEM. NAME |
|---|---|---|---|---|---|---|
| 1 | 330500 | −3.30 | 12 | 0.387 | 43 | Macbecin II |
| 2 | 118994 | −2.60 | 14 | 0.332 | 43 | Diglycoaldehyde |
| 3 | 366140 | −3.20 | 15 | 0.280 | 43 | Pyrazoloacridine |
| 4 | 153858 | −4.00 | 15 | 0.275 | 43 | Maytansine |
| 5 | 268242 | −4.30 | 15 | 0.264 | 43 | N N-Dibenzyldaunomycin |
| 6 | 67574 | −3.00 | 62 | 0.259 | 43 | Vincristine Sulfate |
| 7 | 267213 | −2.90 | 15 | 0.245 | 43 | Glyoxalic Alkylat. Deriv. |
| 8 | 409962 | −3.30 | 132 | 0.236 | 43 | BCNU |
| 9 | 332598 | −9.00 | 9 | 0.222 | 43 | Rhizoxin |
| 10 | 71851 | −2.30 | 15 | 0.207 | 43 | A-TGDR |
| 11 | 102627 | −2.00 | 15 | 0.187 | 43 | Yoshi-864 |

TABLE 4

COMPARE CORR LC50
PARENT = NSC S 695032 LCONC = −4.30 M (BV)
PEARSON

|   | LNC | LCONC | (MAX X) | CORR. COEFF. | (N) | CHEM. NAME |
|---|---|---|---|---|---|---|
| 1 | 740 | −3.60 | 131 | | 46 | Methotrexate |
| 2 | 750 | −3.60 | 59 | | 46 | Busulfan |
| 3 | 752 | −3.60 | 132 | | 46 | Thioguanine |
| 4 | 755 | −3.12 | 132 | | 46 | 6-Mercaptopurine |
| 5 | 762 | −3.30 | 63 | | 46 | Nitrogen Mustard |
| 6 | 1895 | −2.00 | 15 | | 46 | Guanazole |
| 7 | 3051 | −2.00 | 15 | | 46 | N-Methylformamide |
| 8 | 3053 | −6.60 | 72 | | 46 | Actinomycin D |
| 9 | 3088 | −3.12 | 125 | | 46 | Chlorambucil |
| 10 | 4728 | −2.30 | 15 | | 46 | Thiadiazole |
| 11 | 6396 | −3.00 | 125 | | 46 | Thio-Tepa |

The data in Tables 2–4 indicate that curazole exhibits an antimitotic mode of action. This is because most of the drugs exhibiting mean-graph profiles similar to curazole (as tabulated in Tables 2–4) are antimitotics.

Examples 64–123

Figure 4:
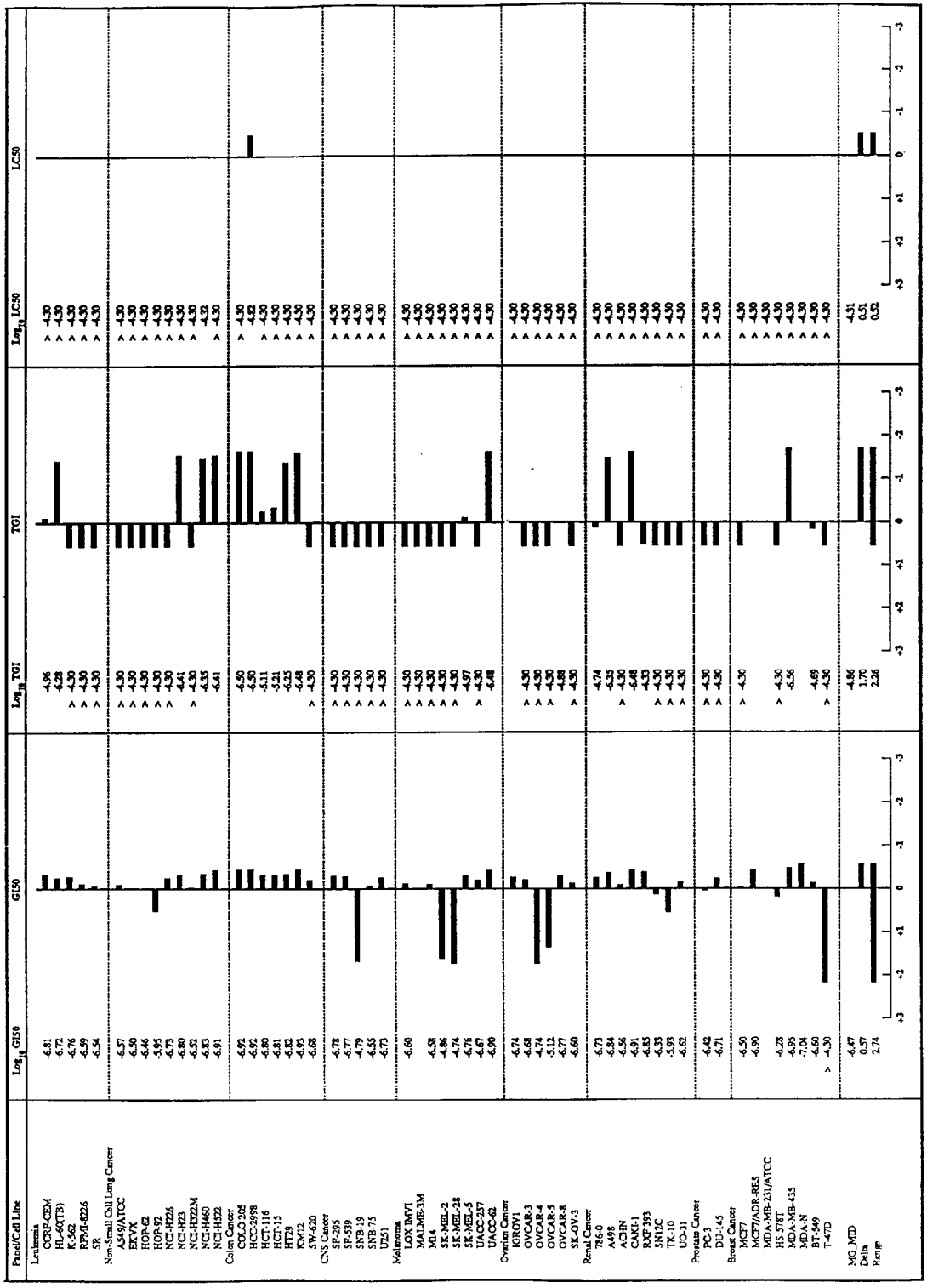
FIG. 4 shows mean plots of data from FIGS. 3A–3I, arranged similarly to the plots shown in FIG. 2.
Figure 5:
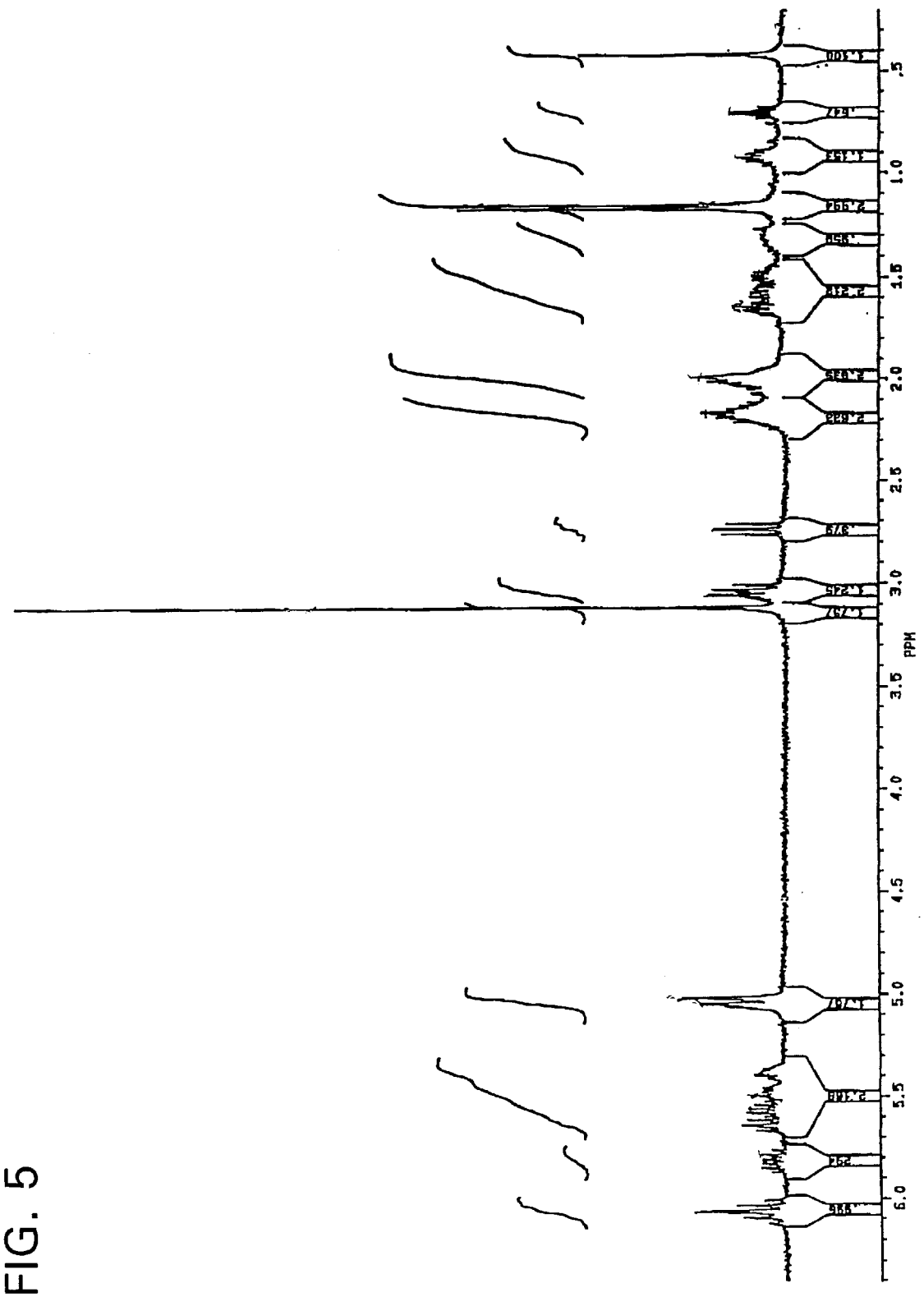
FIG. 5 is an NMR spectrum of curacin D.
Figure 6:
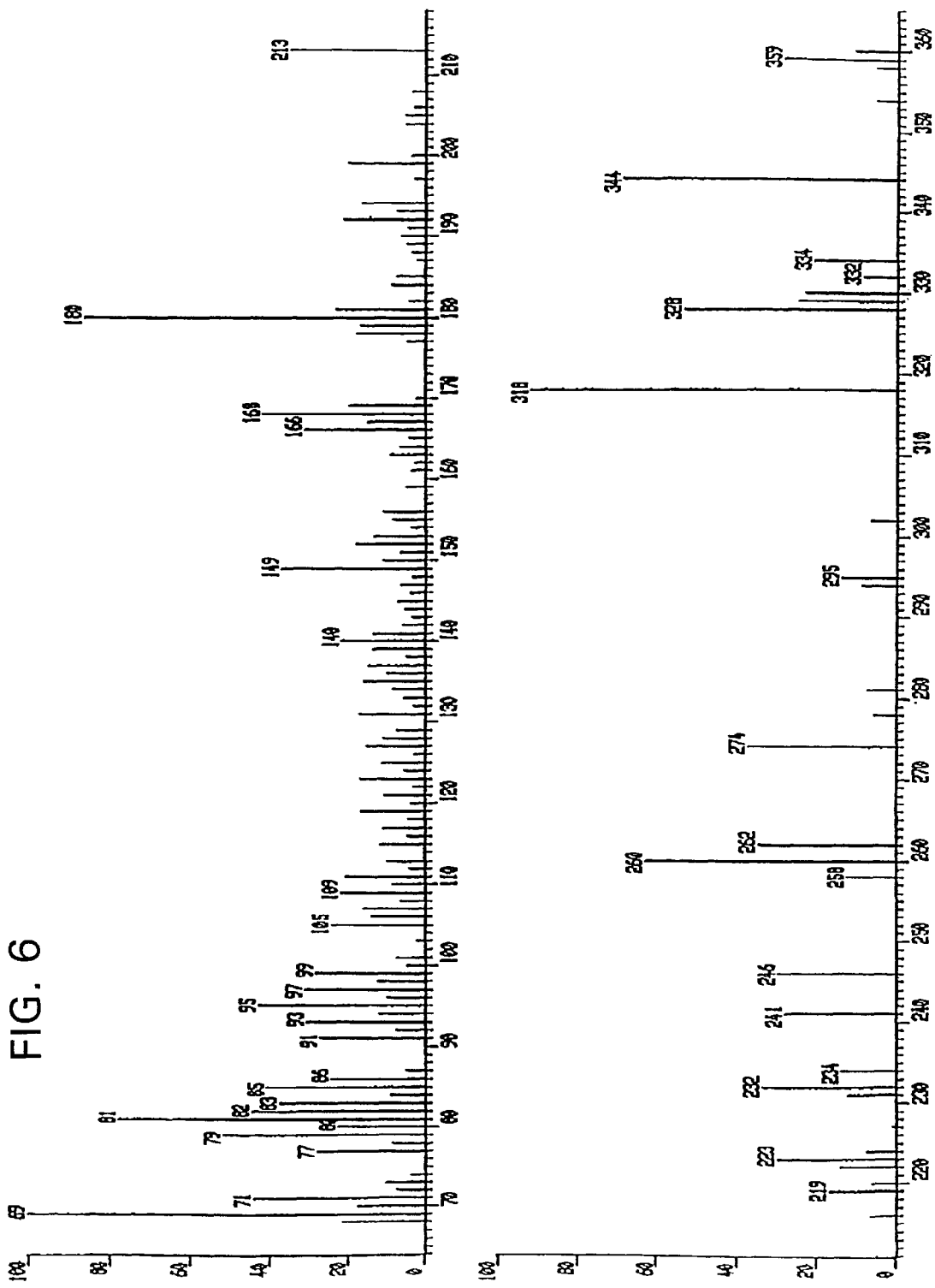
FIG. 6 is a mass spectrum of curacin D.
Figure 7:
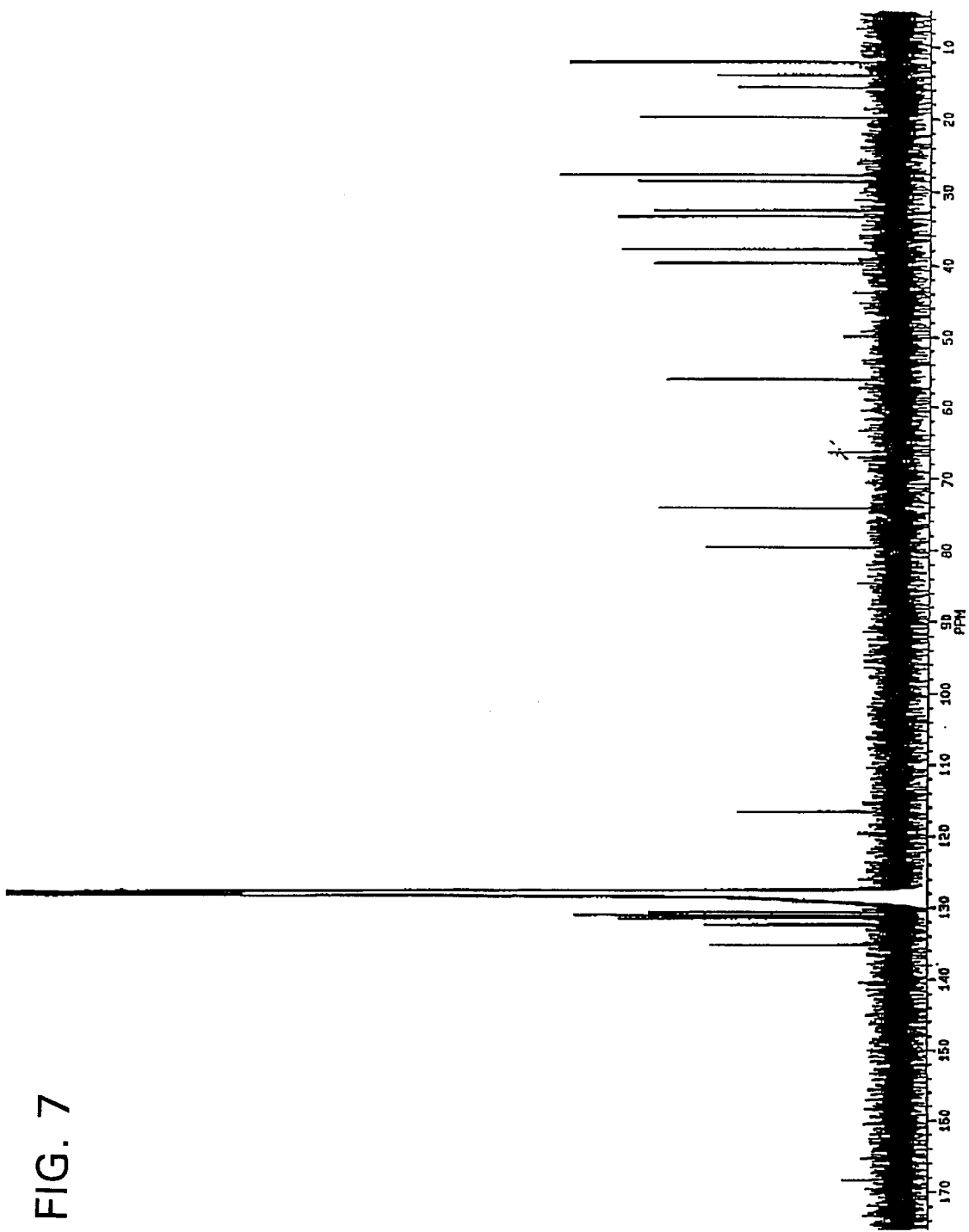
FIG. 7 is a $^{13}C$ NMR spectrum of curacin D.

In these Examples, purified curazole was tested according to the 60-cell line assay described above in Examples 4–63. Dose-response data are shown in FIGS. 3A–3I, and mean-plot data are shown in FIG. 4.

Again, these data indicate that curazole functions as an antimitotic and has a mode of action similar to a number of conventional antineoplastics.

The present invention has been described with reference to certain preferred embodiments. A person of ordinary skill in the art will understand that the invention can depart from these preferred embodiments and still be within the scope of the following claims.

We claim:

1. A compound according to the formula

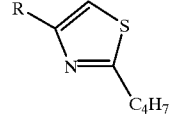

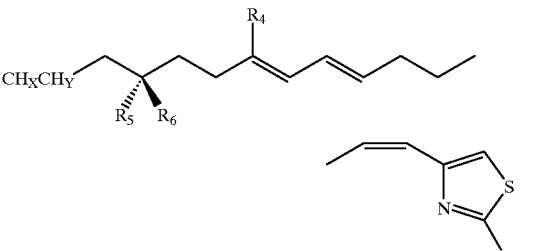

wherein $R_4$ is a hydrogen or a lower alkyl, $R_5$ is selected from the group consisting of a hydrogen, a hydroxyl, a lower alkyl, and a lower alkoxy, $R_6$ is selected from the group consisting of hydrogen, a hydroxyl, lower alkyl, and a lower alkoxy, or wherein $R_5$ and $R_6$ are bonded together to form a ring structure having from three to six atoms in the ring, and wherein X is 2 or 3 and Y is 1 or 2.

2. The compound according to claim 1, selected from the group consisting of

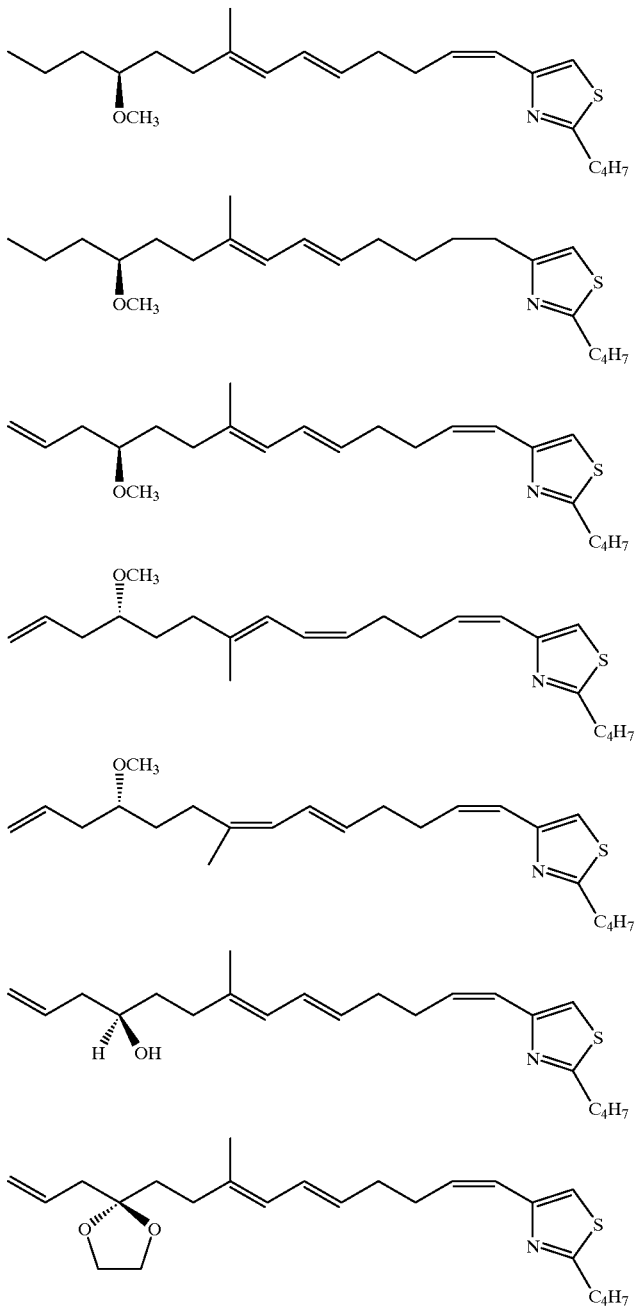

3. The compound according to claim 1 wherein R satisfies the formula

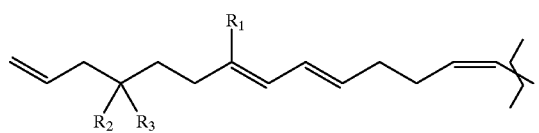

wherein $R_1$ is selected from the group consisting of hydrogen and lower alkyl; $R_2$ is selected from the group consisting of hydrogen, hydroxyl, lower alkyl, and lower alkoxy; $R_3$ is selected from the group consisting of hydrogen, hydroxyl, lower alkyl, and lower alkoxy, or $R_2$ and $R_3$ are bonded together to form a cyclic ring structure having from 3 to about 6 atoms in the ring.

4. The compound according to claim 3 wherein $R_1$ is hydrogen or methyl.

5. The compound according to claim 3 wherein $R_2$ is selected from the group consisting of hydrogen, hydroxyl, and methoxy.

6. The compound according to claim 3 wherein $R_3$ is selected from the group consisting of hydrogen, hydroxyl, and methoxy.

7. Curazole and steroisomers thereof having the formula

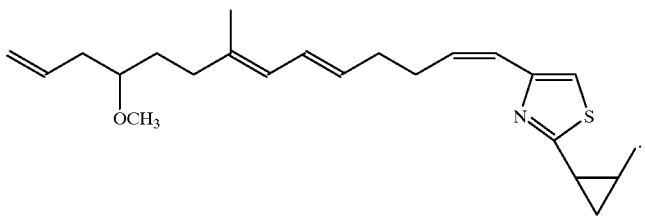

8. A composition comprising an effective amount of a compound according to the formula

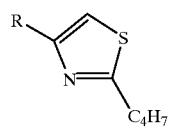

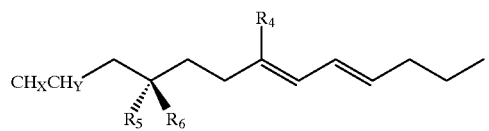

-continued

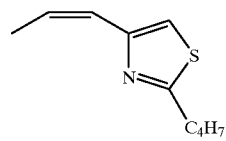

wherein $R_4$ is a hydrogen or a lower alkyl, $R_5$ is selected from the group consisting of a hydrogen, a hydroxyl, a lower alkyl, and a lower alkoxy, $R_6$ is selected from the group consisting of a hydrogen, a hydroxyl, a lower alkyl, and a lower alkoxy, or wherein $R_5$ and $R_6$ are bonded together to form a ring structure having from three to six atoms in the ring, and wherein X is 2 or 3 and Y is 1 or 2.

9. The composition according to claim 8 comprising a sufficient amount of the compound to act as an antiproliferative agent to living cells.

10. The composition according to claim 9 wherein the compound is curazole and/or a stereoisomer thereof.

* * * * *

UNITED STATES PATENT AND TRADEMARK OFFICE
CERTIFICATE OF CORRECTION

PATENT NO. : 6,057,348
DATED : May 2, 2000
INVENTOR(S) : Gerwick et al.

It is certified that error appears in the above-identified patent and that said Letters Patent is hereby corrected as shown below:

| Col./Line | Error Reads | Should Read |
|---|---|---|
| Cover, Assignee | *ADD:* | The University of Texas System, Austin, Tex. |
| 2/13 | in , | in |
| 3/49 | left-hand and mean | left-hand mean |
| 10/55 | *ADD:* | Formula 13 |
| 13/8 | $C_3H_7$ | $C_4H_7$ |
| 15/21 | 47 , | 47 |
| 20/40 | *DELETE FORMULA* | |
| 20/62 | of hydrogen | of a hydrogen |
| 20/62 | lower alkyl | a lower alkyl |
| 22/68 | steroisomers | stereoisomers |
| 23/16 | *DELETE FORMULA* | |

Signed and Sealed this

Twenty-second Day of May, 2001

Attest:

NICHOLAS P. GODICI

*Attesting Officer*  *Acting Director of the United States Patent and Trademark Office*